United States Patent [19]

Civelli et al.

[11] Patent Number: 5,441,883

[45] Date of Patent: Aug. 15, 1995

[54] A3 ADENOSINE RECEPTOR, DNA, AND USES

[75] Inventors: Olivier Civelli; Qun-Yong Zhou, both of Portland, Oreg.

[73] Assignee: State of Oregon, Acting by and Through the Oregon State Board of Higher Education on Behalf of the Oregon Health Sciences University, Portland, Oreg.

[21] Appl. No.: 101,435

[22] Filed: Aug. 2, 1993

Related U.S. Application Data

[63] Continuation of Ser. No. 847,563, Mar. 3, 1992, abandoned.

[51] Int. Cl.⁶ .............................................. C12N 15/12
[52] U.S. Cl. .................................. 435/257.13; 435/6; 435/69.1; 435/320.1; 536/23.5; 536/24.31
[58] Field of Search ................ 435/69.1, 252.7, 320.1; 530/350; 536/23.5

[56] References Cited

PUBLICATIONS

Ribeiro & Sebastiao, 1986, "Adenosine receptors and calcium: basis for proposing a third (A3) adenosine receptor", Prog. Neurobiol. 26: 179-209.

Stiles, 1986, "Novel adenosine receptors", Trends Pharmacol. Sci. 7: 486-490.

Williams, 1987, "Purine receptors in mammalian tissues: pharmacology and functional significance", Ann. Rev. Pharmacol. Toxicol. 27: 315-345.

Ramkumar et al., 1988, "Adenosine receptors: clinical implications and biochemical mechanisms", Prog. Drug. Res. 32: 195-247.

Fredholm & Dunwiddie, 1988, "How does adenosine inhibit transmitter release?", Trends Pharmacol. Sci. 9: 130-134.

Nakata, 1989, "Purification of A1 adenosine receptor from rat brain membranes", J. Biol. Chem. 264: 16545-16551.

Libert et al., 1989, "Selective amplification and cloning of four new members of the G protein-coupled receptor family", Science 244: 569-72.

Olah et al., 1990, "Purification and characterization of bovine cerebral cortex A1 adenosine receptor", Arch. Biochem. Biophys. 283: 440-446.

Maenhaut et al., 1990, "RDC8 codes for an adenosine A2 receptor with physiological constitutive activity", Biochem. Biophys. Res. Commun. 173: 1169-1178.

Ali et al., 1990, "Activation of phospholipase C via adenosine receptors provides synergistic signals for secretion in antigen-stimulated RBL-2H3 cells. Evidence for a novel adenosine receptor", J. Biol. Chem. 265: 745-753.

Zhou et al., 1990, "Cloning and expression of human and rat D1 dopamine receptors", Nature 347: 76-80.

Sebastiao et al., 1990, "The inhibitory adenosine receptor at the neuromuscular junction and hippocampus of the rat: antagonism by 1,3,8-substituted xanthines", Br. J. Pharmacol. 100: 55-62.

Stiles, 1990, "Adenosine receptors and beyond: molecular mechanisms of physiological regulation", Clin. Res. 38: 10-18.

(List continued on next page.)

Primary Examiner—Garnette D. Draper
Assistant Examiner—John D. Ulm
Attorney, Agent, or Firm—Allegretti & Witcoff, Ltd.

[57] ABSTRACT

The present invention relates to a novel mammalian adenosine receptor. The invention is directed toward the isolation, characterization and pharmacological use of the rat A3 adenosine receptor, the gene corresponding to this receptor, a recombinant eukaryotic expression construct capable of expressing the rat A3 adenosine receptor in cultures of transformed eukaryotic cells and such cultures of transformed eukaryotic cells that synthesize the rat A3 adenosine receptor. The invention also provides methods for screening adenosine-receptor agonists and antagonists in vitro using preparations of the rat A3 adenosine receptor from such cultures of eukaryotic cells transformed with a recombinant eukaryotic expression construct comprising the rat A3 adenosine receptor gene.

7 Claims, 14 Drawing Sheets

```
GAAGCCCTGTCTCTGTCTGCCCAGGGAAGTAAGAACAGC      39
AGCACTCTTGGATTTGGCTGCATAGAACTGTGTCCTCCA      78
GGTTATCAGGAGGGCAGGGCTAAGTGGCTGAGGTCTAC     116
GATCCTGTCAAGGACCTTTTCTGAGAAAAGTCTCTAAAA    155
GAGCATCACACCAGAAGGAATAAGCAAGTCATGAATTC     193
TCCGGACTGTTGCTACCTTCTAACTTCTGGGCAGATGT     231
CTGTCAAGAGCTAGGTCCACTGGCCCATACACATCCTGC    270
TGAAGAAGCAACAGAAGTTTCCAGCTGAAGCTTCTCTGA   309

GACAGC  ATG  AAA  GCC  AAC  AAT  ACC  ACG  ACG   339
        MET  Lys  Ala  Asn  Asn  Thr  Thr  Thr    8

AGT  GCC  TTG  TGG  TTG  CAA  ATC  ACC  TAC  GTC   369
Ser  Ala  Leu  Trp  Leu  Gln  Ile  Thr  Tyr  Val   18

ACC  ATG  GAG  GCT  GCC  ATT  GGT  CTC  TGT  GCT   399
Thr  MET  Glu  Ala  Ala  Ile  Gly  Leu  Cys  Ala   28

GTA  GTG  GGC  AAC  ATG  CTG  GTC  ATC  TGG  GTG   429
Val  Val  Gly  Asn  MET  Leu  Val  Ile  Trp  Val   38

GTC  AAG  CTG  AAC  CGC  ACT  CTG  AGG  ACC  ACC   459
Val  Lys  Leu  Asn  Arg  Thr  Leu  Arg  Thr  Thr   48
```

OTHER PUBLICATIONS

Nakahata et al., 1991, "Adenosine inhibits histamine-induced phosphoinositide hydrolysis mediated via pertussis toxin-sensitive G protein in human astrocytoma cells", J. Neurochem. 57: 963–969.

Meyerhof et al., 1991, "Molecular cloning of a novel putative G-protein coupled receptor expressed during rat spermiogenesis", FEBS Lett. 284: 155–160.

Oliveira et al., 1991, "Solubilized rat brain adenosine receptors have two high-affinity binding sites for 1,3-dipropyl-8-cyclopentylxanthine", J. Neurochem. 57: 1165–1171.

Libert et al., 1991, "The orphan receptor cDNA RDC7 encodes an A1 adenosine receptor", EMBO J. 10: 1677–1682.

Mahan et al., 1991, "Cloning and expression of an A1 adenosine receptor from rat brain", Molecular Pharmacol. 40: 1–7.

Reppert et al., 1991, "Molecular cloning and characterization of a rat A1-adenosine receptor that is widely expressed in brain and spinal cord", Molec. Endo. 5: 1037–1048.

Lin et al., 1991, "2-Chloroadenosine decreases tyrosylprotein sulfotransferase activity in the Golgi apparatus in PC12 cells. Evidence for a novel receptor", J. Biol. Chem. 266: 14457–14463.

FIG. 1A

| | |
|---|---:|
| GAAGCCCTGTCTCTGTCTGCCCAGGGAAGTAAGAACAGC | 39 |
| AGCACTCTTGGATTTGGCTGCATAGAACTGTGTCCTCCA | 78 |
| GGTTATCAGGAGGGCAGGGCTAAGTGGCTGAGGTCTAC | 116 |
| GATCCTGTCAAGGACCTTTTCTGAGAAAGTCTCTAAAA | 155 |
| GAGCATCACACCAGAAGGAATAAGCAAGTCATGAATTC | 193 |
| TCCGGACTGTTGCTACCTTCTAACTTCTGGGCAGATGT | 231 |
| CTGTCAAGAGCTAGGTCCACTGGCCCATACACATCCTGC | 270 |
| TGAAGAAGCAACAGAAGTTTCCAGCTGAAGCTTCTCTGA | 309 |

```
GACAGC  ATG  AAA  GCC  AAC  AAT  ACC  ACG  ACG    339
        MET  Lys  Ala  Asn  Asn  Thr  Thr  Thr      8
                       *    *

AGT  GCC  TTG  TGG  TTG  CAA  ATC  ACC  TAC  GTC    369
Ser  Ala  Leu  Trp  Leu  Gln  Ile  Thr  Tyr  Val    18
                                  I

ACC  ATG  GAG  GCT  GCC  ATT  GGT  CTC  TGT  GCT    399
Thr  MET  Glu  Ala  Ala  Ile  Gly  Leu  Cys  Ala    28

GTA  GTG  GGC  AAC  ATG  CTG  GTC  ATC  TGG  GTG    429
Val  Val  Gly  Asn  MET  Leu  Val  Ile  Trp  Val    38

GTC  AAG  CTG  AAC  CGC  ACT  CTG  AGG  ACC  ACC    459
Val  Lys  Leu  Asn  Arg  Thr  Leu  Arg  Thr  Thr    48
                              #
```

FIG. 1B

```
ACC TTC TAT TTC ATC GTC TCC CTA GCA CTG   489
Thr Phe Tyr Phe Ile Val Ser Leu Ala Leu    58
     II

GCA GAC ATT GCT GTT GGG GTG CTG GTC ATA   519
Ala Asp Ile Ala Val Gly Val Leu Val Ile    68

CCC TTG GCC ATT GCC GTC AGC CTG GAG GTC   549
Pro Leu Ala Ile Ala Val Ser Leu Glu Val    78

CAG ATG CAC TTC TAT GCC TGC CTT TTC ATG   579
Gln MET His Phe Tyr Ala Cys Leu Phe MET    88
                         III

TCC TGT GTG CTT CTG GTC TTC ACC CAT GCT   609
Ser Cys Val Leu Leu Val Phe Thr His Ala    98

TCC ATC ATG TCC TTG CTG GCC ATT GCT GTA   639
Ser Ile MET Ser Leu Leu Ala Ile Ala Val   108

GAC CGA ATC CTG CGA GTC AAG CTG ACA GTC   669
Asp Arg Tyr Leu Arg Val Lys Leu Thr Val   118
                                  #

AGA TAT AGA ACG GTT ACC ACT CAA AGA AGA   699
Arg Tyr Arg Thr Val Thr Thr Gln Arg Arg   128
                             #

ATA TGG CTA TTC CTG GGC CTC TGC TGG CTA   729
Ile Trp Leu Phe Leu Gly Leu Cys Trp Leu   138
 IV

GTG TCC TTT CTG GTG GGA CTG ACC CCC ATG   759
Val Ser Phe Leu Val Gly Leu Thr Pro MET   148
```

FIG. 1C

| | | | | | | | | | | |
|---|---|---|---|---|---|---|---|---|---|---|
| TTT | GGC | TGG | AAT | AGA | AAA | GTG | ACC | TTA | GAG | 789 |
| Phe | Gly | Trp | Asn | Arg | Lys | Val | Thr | Leu | Glu | 158 |
| IV | | | | | | | | | | |

| | | | | | | | | | | |
|---|---|---|---|---|---|---|---|---|---|---|
| CTC | TCT | CAA | AAC | AGC | TCC | ACC | CTC | TCA | TGC | 819 |
| Leu | Ser | Gln | Asn | Ser | Ser | Thr | Leu | Ser | Cys | 168 |

| | | | | | | | | | | |
|---|---|---|---|---|---|---|---|---|---|---|
| CAC | TTC | CGT | TTC | GTG | GTC | GGC | TTG | GAT | TAC | 849 |
| His | Phe | Arg | Phe | Val | Val | Gly | Leu | Asp | Tyr | 178 |
| | | | | | | | | | V | |

| | | | | | | | | | | |
|---|---|---|---|---|---|---|---|---|---|---|
| ATG | GTC | TTC | TTC | AGC | TTC | ATC | ACC | TGG | ATC | 879 |
| MET | Val | Phe | Phe | Ser | Phe | Ile | Thr | Trp | Ile | 188 |

| | | | | | | | | | | |
|---|---|---|---|---|---|---|---|---|---|---|
| CTC | ATC | CCC | CTG | GTT | GTC | ATG | TGC | ATC | ATC | 909 |
| Leu | Ile | Pro | Leu | Val | Val | MET | Cys | Ile | Ile | 198 |

| | | | | | | | | | | |
|---|---|---|---|---|---|---|---|---|---|---|
| TAT | CTG | GAC | ATC | TTC | TAC | ATC | ATC | CGA | AAC | 939 |
| Tyr | Leu | Asp | Ile | Phe | Tyr | Ile | Ile | Arg | Asn | 208 |

| | | | | | | | | | | |
|---|---|---|---|---|---|---|---|---|---|---|
| AAA | CTC | AGT | CAG | AAT | CTG | ACT | GGC | TTC | AGA | 969 |
| Lys | Leu | Ser | Gln | Asn | Leu | Thr | Gly | Phe | Arg | 218 |

| | | | | | | | | | | |
|---|---|---|---|---|---|---|---|---|---|---|
| GAG | ACG | CGT | GCA | TTT | TAC | GGT | CGG | GAG | TTC | 999 |
| Glu | Thr | Arg | Ala | Phe | Tyr | Gly | Arg | Glu | Phe | 228 |

| | | | | | | | | | | |
|---|---|---|---|---|---|---|---|---|---|---|
| AAG | ACC | GCT | AAG | TCC | CTG | TTT | CTG | GTT | CTC | 1029 |
| Lys | Thr | Ala | Lys | Ser | Leu | Phe | Leu | Val | Leu | 238 |
| | | | | VI | | | | | | |

| | | | | | | | | | | |
|---|---|---|---|---|---|---|---|---|---|---|
| TTC | TTG | TTT | GCC | TTG | TGC | TGG | CTG | CCT | TTG | 1059 |
| Phe | Leu | Phe | Ala | Leu | Cys | Trp | Leu | Pro | Leu | 248 |

| | | | | | | | | | | |
|---|---|---|---|---|---|---|---|---|---|---|
| TCC | ATC | ATC | AAT | TTT | GTT | TCC | TAC | TTT | AAT | 1089 |
| Ser | Ile | Ile | Asn | Phe | Val | Ser | Tyr | Phe | Asn | 258 |

FIG. 1D

| | | | | | | | | | | |
|---|---|---|---|---|---|---|---|---|---|---|
| GTG | AAG | ATA | CCA | GAG | ATT | GCA | ATG | TGC | CTG | 1119 |
| Val | Lys | Ile | Pro | Glu | Ile | Ala | MET | Cys | Leu | 268 |
| VI  |     |     |     |     | VII |     |     |     |     |      |

| | | | | | | | | | |
|---|---|---|---|---|---|---|---|---|---|
| GGC | ATC | CTG | TTG | TCC | CAT | GCG | AAC | TCC | ATG | 1149 |
| Gly | Ile | Leu | Leu | Ser | His | Ala | Asn | Ser | MET | 278 |

| | | | | | | | | | |
|---|---|---|---|---|---|---|---|---|---|
| ATG | AAC | CCT | ATT | GTC | TAC | GCC | TGC | AAA | AAT | 1179 |
| MET | Asn | Pro | Ile | Val | Tyr | Ala | Cys | Lys | Asn | 288 |

| | | | | | | | | | |
|---|---|---|---|---|---|---|---|---|---|
| AAA | AAA | GTT | CAA | AGA | AAC | CAC | TTT | GTG | ATC | 1209 |
| Lys | Lys | Val | Gln | Arg | Asn | His | Phe | Val | Ile | 298 |

| | | | | | | | | | |
|---|---|---|---|---|---|---|---|---|---|
| CTC | AGA | GCT | TGC | AGG | CTC | TGT | CAG | ACC | TCG | 1239 |
| Leu | Arg | Ala | Cys | Arg | Leu | Cys | Gln | Thr | Ser | 308 |

| | | | | | | | | | |
|---|---|---|---|---|---|---|---|---|---|
| GAT | TCT | TTG | GAC | TCA | AAC | CTT | GAA | CAG | ACT | 1269 |
| Asp | Ser | Leu | Asp | Ser | Asn | Leu | Glu | Gln | Thr | 318 |
|     |     |     |     | #   |     |     |     |     |     |      |

| | | |
|---|---|---|
| ACT | GAG | TAGTTACCATGACAGATAAAGAGCCAGCTC | 1305 |
| Thr | Glu |                                | 320  |

ATTTACCTTCACAGTTCGCATCGGTAAACACTATAAGGA 1344

CTTAACAGCCATTCTTGCTTACTTCCACTGCAGTGGGAT 1383

CATCGGGCTGGTTGCCACAGAGCTCCCTTCCCTCCTCCC 1422

TCCGCTCCTCCCTCCACTCCTCCCTCCGCTCCTCCCTTCC 1462

CTCCTCCCTCTGCTCCCTCCCTCCAGTCTTCCCTCCACTC 1502

CTCCCTCCCGCCTTCATGTATTTTCTTGAGCTTCTCTCATT 1543

CAATTCTGTGGAGGTCTGACATGAAGGCAATGCATTCCT 1582

FIG. 1E

```
GGTTACCACAGACTTCGCCCTTCCTTCCCAGACACAAGA   1621

AGTAATGGAGTGAATGTTGAGGGAGTCTCCTCTCACTAA   1660

AGAAGACTCTAGTGGGGCTGGATGTACAGAACCTGCGTT   1699

GAAGGATCCTAGGATGTTGGGAACACAGGGAGTGAATTG   1738

AATTTAAAGAGGGCTAAATTCACCTGTGTGGGTGCATTT   1777

GAGCAAATAAAGATGGCGCCCAAAAAAAAAAAAAAAA    1815

AAAAAAAAAAAAAAA                          1831
```

FIG. 2A

```
                 I
R226  MKANNTTTSALWLQITY VTME AAIG-L CAVVGNMLVI WVVKLN
A1                      MPPAISAFQAAYIGIEVLIA-LVSVPGNVLVI WAVKVN
A2                      MSTMGSW---VY ITVEL AIAVL- AILGNVLQ WAVWLN

II
R226  RT LR TT FY FIVSLAL ADI AVGVL VIP LAIAVSLEVQMHFYAC
A1    QA LR DA TF CFIVSLAV ADV AVGAL VIP LAILINIGPRTYFHTC
A2    SN LQ NV TN YFVVSLAA ADI AVGV LAI PFAITISTGFCAACHNC

III
R226  LFMS C VL LV FTHAS IMS LLAIA VDRYLR VKLTV RYRTVTTQRR
A1    LMVA C PV LI LTQSS ILA LLAIA VDRYLR VKIPL RYKTVVTPRR
A2    LFFA C FV L LTQSS IFS LLAIA IDRYI AIRIP LRYNGLVTGTR

IV
R226  IWLFLGLCWL VS FLVGLTPMFGWN RKVTLELSQNSST-----
A1    AAVAIAGCWIL SFVVGLTPLFGWN RLGEAQRAWAANGSGGEPV
A2    AKGIIAVCWVL SFAIGLTPMLGWN NCSQPKEGRNYSQGCGEGQ
```

FIG. 2B

```
                                       V
R226   LSCHFRFVVGLDYMVFFSFITWILIPLVVMCIIYLDIFYIIRN
A1     IKCEFEKVISMEYMVYFNFFVWVLPPLLLMVLIYLEVFYLIRR
A2     VACLFEDVVPMNYMVYNFFAFVLVPLLLMLGVYLRIFLAARR

VI
R226   KLSQNLTG--FRETRA-FYGREFKTAKSLFLVLFLFALQWLPL
A1     QLGKKVSA--SSGDPQKYYGKELKIAKSLALILFALSWLPL
A2     QLKQMESQPLPGERARSTLQKEVHAAKSLAIIVGLFALQWLPL

VI                              VII
R226   SIINFVSYFNVKIPE--IAMCLGILLSHANSMMNPIVYACKIK
A1     HILNCITLFCPSCRKPSILMYIAIFLTHGNSAMNPIVYAFRIQ
A2     HIINCFTFCPECSHAPLWLMYLTIVLSHTNSVVNPFIYAYRIR

R226   KFKETYFVILRACRLCQTSDSLDSNLEQTTE      320
A1     KFRVTFLKIWNDHFRCQPTPPVDEDPPEEAPHD    326
A2     EERQTFRKIIRSHVLRRREPFKAGGTSARALAAHGSDGEQISL
```

FIG. 2C

A2  RLNGHPPGVWANGSAPHPERRPNGYTLGLVSGGIAPESHGDMG

A2  LPDVELLSHELKGACPESPPGLEGPLAQDGAGV  411

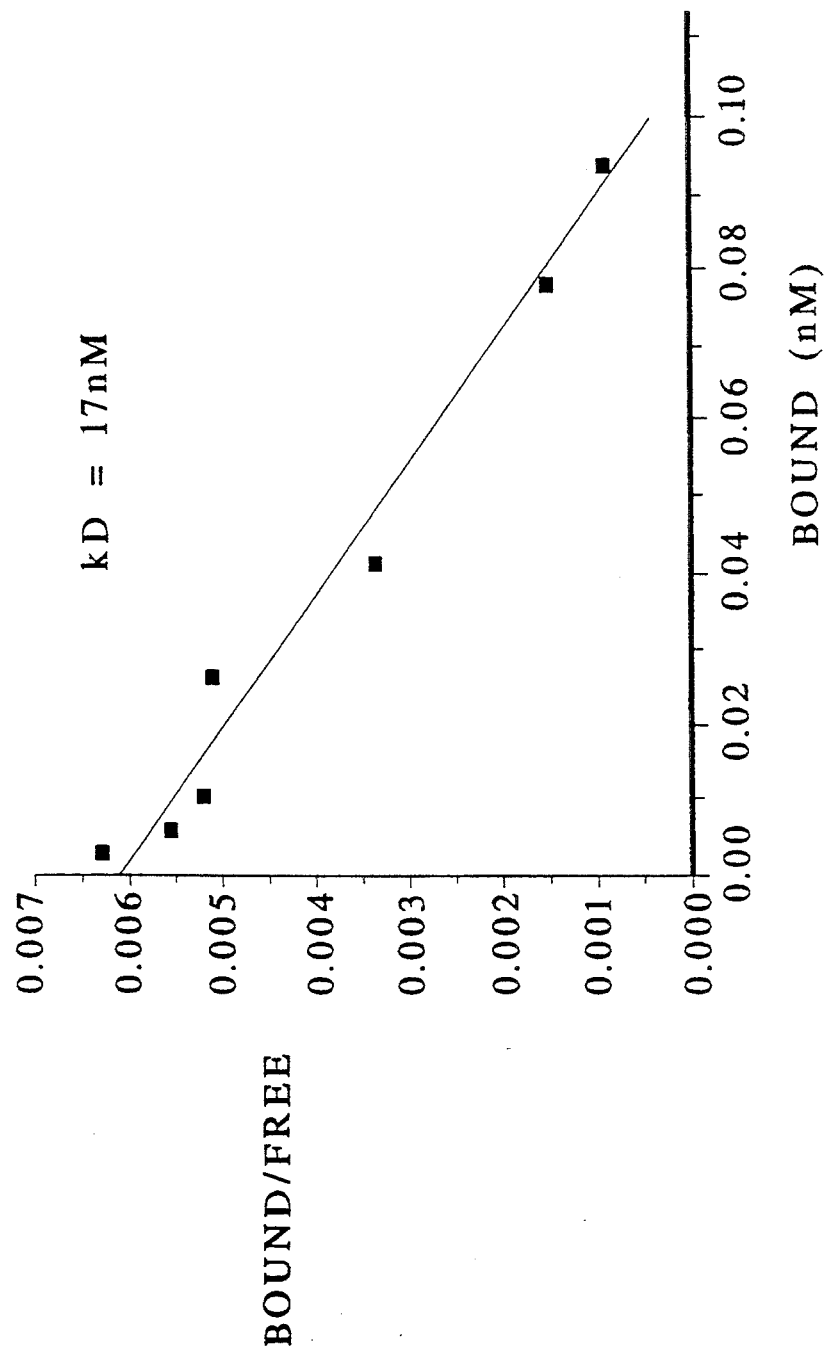

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: modified_base
    ( B ) LOCATION: 23..24
    ( D ) OTHER INFORMATION: /mod_base=i ( x i ) SEQUENCE DESCRIPTION: SEQ ID NO:1:

GAGTCGACCT GTGYGYSATY RCNNTKGACM GSTAC           35

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: modified_base
        ( B ) LOCATION: 18
        ( D ) OTHER INFORMATION: /mod_base=i ( i x ) FEATURE:
        ( A ) NAME/KEY: modified_base
        ( B ) LOCATION: 27
        ( D ) OTHER INFORMATION: /mod_base=i ( x i ) SEQUENCE DESCRIPTION: SEQ ID NO:2:

CAGAATTCAG W AGGGCANCC AGCAGANSRY GAA           33

( 2 ) INFORMATION FOR SEQ ID NO:3:

( i ) SEQUENCE CHARACTERISTICS:
        ( A ) LENGTH: 1831 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 316..1276

( x i ) SEQUENCE DESCRIPTION: SEQ ID NO:3:

```
GAAGCCCTGT CTCTGTCTGC CAGGGAAGT  AAGAACAGCA GCACTCTTGG ATTTGGCTGC         60

ATAGAACTGT GTCCTCCAGG TTATCAGGAG GGCAGGGCTA AGTGGCTGAG GTCTACGATC        120

CTGTCAAGGA CCTTTTCTGA GAAAAGTCTC TAAAAGAGCA TCACACCAGA AGGAATAAGC        180

AAGTCATGAA TTCTCCGGAC TGTTGCTACC TTCTAACTTC TGGGCAGATG TCTGTCAAGA        240

GCTAGGTCCA CTGGCCCATA CACATCCTGC TGAAGAAGCA ACAGAAGTTT CCAGCTGAAG        300

CTTCTCTGAG ACAGC ATG AAA GCC AAC AAT ACC ACG ACG AGT GCC TTG TGG        351
                 Met Lys Ala Asn Asn Thr Thr Thr Ser Ala Leu Trp
                  1               5                  10

TTG CAA ATC ACC TAC GTC ACC ATG GAG GCT GCC ATT GGT CTC TGT GCT         399
Leu Gln Ile Thr Tyr Val Thr Met Glu Ala Ala Ile Gly Leu Cys Ala
         15                  20                  25

GTA GTG GGC AAC ATG CTG GTC ATC TGG GTG GTC AAC CTG AAC CGC ACT         447
Val Val Gly Asn Met Leu Val Ile Trp Val Val Asn Leu Asn Arg Thr
     30                  35                  40

CTG AGG ACC ACC ACC TTC TAT TTC ATC GTC TCC CTA GCA CTG GCA GAC         495
Leu Arg Thr Thr Thr Phe Tyr Phe Ile Val Ser Leu Ala Leu Ala Asp
 45                  50                  55                  60

ATT GCT GTT GGG GTG CTG GTC ATA CCC TTG CCC ATT GCC GTC AGC CTG         543
Ile Ala Val Gly Val Leu Val Ile Pro Leu Pro Ile Ala Val Ser Leu
             65                  70                  75
```

| | | | | | | | | | | | | | | | | |
|---|---|---|---|---|---|---|---|---|---|---|---|---|---|---|---|---|
| GAG | GTC | CAG | ATG | CAC | TTC | TAT | GCC | TGC | CTT | TTC | ATG | TCC | TGT | GTG | CTT | 591 |
| Glu | Val | Gln | Met | His | Phe | Tyr | Ala | Cys | Leu | Phe | Met | Ser | Cys | Val | Leu | |
| | | | 80 | | | | | 85 | | | | | 90 | | | |
| CTG | GTC | TTC | ACC | CAT | GCT | TCC | ATC | ATG | TCC | TTG | CTG | GCC | ATT | GCT | GTA | 639 |
| Leu | Val | Phe | Thr | His | Ala | Ser | Ile | Met | Ser | Leu | Leu | Ala | Ile | Ala | Val | |
| | | 95 | | | | | 100 | | | | | 105 | | | | |
| GAC | CGA | TAC | CTG | CGA | GTC | AAG | CTG | ACA | GTC | AGA | TAT | AGA | ACG | GTT | ACC | 687 |
| Asp | Arg | Tyr | Leu | Arg | Val | Lys | Leu | Thr | Val | Arg | Tyr | Arg | Thr | Val | Thr | |
| | 110 | | | | | 115 | | | | | 120 | | | | | |
| ACT | CAA | AGA | AGA | ATA | TGG | CTA | TTC | CTG | GGC | CTC | TGC | TGG | CTA | GTG | TCC | 735 |
| Thr | Gln | Arg | Arg | Ile | Trp | Leu | Phe | Leu | Gly | Leu | Cys | Trp | Leu | Val | Ser | |
| 125 | | | | | 130 | | | | | 135 | | | | | 140 | |
| TTT | CTG | GTG | GGA | CTG | ACC | CCC | ATG | TTT | GGC | TGG | AAT | AGA | AAA | GTG | ACC | 783 |
| Phe | Leu | Val | Gly | Leu | Thr | Pro | Met | Phe | Gly | Trp | Asn | Arg | Lys | Val | Thr | |
| | | | | 145 | | | | | 150 | | | | | 155 | | |
| TTA | GAG | CTC | TCT | CAA | AAC | AGC | TCC | ACC | CTC | TCA | TGC | CAC | TTC | CGT | TTC | 831 |
| Leu | Glu | Leu | Ser | Gln | Asn | Ser | Ser | Thr | Leu | Ser | Cys | His | Phe | Arg | Phe | |
| | | | 160 | | | | | 165 | | | | | 170 | | | |
| GTG | GTC | GGC | TTG | GAT | TAC | ATG | GTC | TTC | TTC | AGC | TTC | ATC | ACC | TGG | ATC | 879 |
| Val | Val | Gly | Leu | Asp | Tyr | Met | Val | Phe | Phe | Ser | Phe | Ile | Thr | Trp | Ile | |
| | | 175 | | | | | 180 | | | | | 185 | | | | |
| CTC | ATC | CCC | CTG | GTT | GTC | ATG | TGC | ATC | ATC | TAT | CTG | GAC | ATC | TTC | TAC | 927 |
| Leu | Ile | Pro | Leu | Val | Val | Met | Cys | Ile | Ile | Tyr | Leu | Asp | Ile | Phe | Tyr | |
| | 190 | | | | | 195 | | | | | 200 | | | | | |
| ATC | ATC | CGA | AAC | AAA | CTC | AGT | CAG | AAT | CTG | ACT | GGC | TTC | AGA | GAG | ACG | 975 |
| Ile | Ile | Arg | Asn | Lys | Leu | Ser | Gln | Asn | Leu | Thr | Gly | Phe | Arg | Glu | Thr | |
| 205 | | | | | 210 | | | | | 215 | | | | | 220 | |
| CGT | GCA | TTT | TAC | GGT | CGG | GAG | TTC | AAG | ACC | GCT | AAG | TCC | CTG | TTT | CTG | 1023 |
| Arg | Ala | Phe | Tyr | Gly | Arg | Glu | Phe | Lys | Thr | Ala | Lys | Ser | Leu | Phe | Leu | |
| | | | | 225 | | | | | 230 | | | | | 235 | | |
| GTT | CTC | TTC | TTG | TTT | GCC | TTG | TGC | TGG | CTG | CCT | TTG | TCC | ATC | ATC | AAT | 1071 |
| Val | Leu | Phe | Leu | Phe | Ala | Leu | Cys | Trp | Leu | Pro | Leu | Ser | Ile | Ile | Asn | |
| | | | 240 | | | | | 245 | | | | | 250 | | | |
| TTT | GTT | TCC | TAC | TTT | AAT | GTG | AAG | ATA | CCA | GAG | ATT | GCA | ATG | TGC | CTG | 1119 |
| Phe | Val | Ser | Tyr | Phe | Asn | Val | Lys | Ile | Pro | Glu | Ile | Ala | Met | Cys | Leu | |
| | | 255 | | | | | 260 | | | | | 265 | | | | |
| GGC | ATC | CTG | TTG | TCC | CAT | GCG | AAC | TCC | ATG | ATG | AAC | CCT | ATT | GTC | TAC | 1167 |
| Gly | Ile | Leu | Leu | Ser | His | Ala | Asn | Ser | Met | Met | Asn | Pro | Ile | Val | Tyr | |
| | 270 | | | | | 275 | | | | | 280 | | | | | |
| GCC | TGC | AAA | AAT | AAA | AAA | GTT | CAA | AGA | AAC | CAC | TTT | GTG | ATC | CTC | AGA | 1215 |
| Ala | Cys | Lys | Asn | Lys | Lys | Val | Gln | Arg | Asn | His | Phe | Val | Ile | Leu | Arg | |
| 285 | | | | | 290 | | | | | 295 | | | | | 300 | |
| GCT | TGC | AGG | CTC | TGT | CAG | ACC | TCG | GAT | TCT | TTG | GAC | TCA | AAC | CTT | GAA | 1263 |
| Ala | Cys | Arg | Leu | Cys | Gln | Thr | Ser | Asp | Ser | Leu | Asp | Ser | Asn | Leu | Glu | |
| | | | | 305 | | | | | 310 | | | | | 315 | | |
| CAG | ACT | ACT | GAG | T AGTTACCATG ACAGATAAAG AGCCAGCTCA TTTACCTTCA | | | | | | | | | | | | 1316 |
| Gln | Thr | Thr | Glu | | | | | | | | | | | | | |
| | | | 320 | | | | | | | | | | | | | |

```
CAGTTCGCAT CGGTAAACAC TATAAGGACT TAACAGCCAT TCTTGCTTAC TTCCACTGCA      1376

GTGGGATCAT CGGGCTGGTT GCCACAGAGC TCCCTTCCCT CCTCCCTCCG CTCCTCCCTC      1436

CACTCCTCCC TCCGCTCCTC CCTTCCCTCC TCCCTCTGCT CCTCCCTCCA GTCTTCCCTC      1496

CACTCCTCCC TCCCGCCTTC ATGTATTTTC TTGAGCTTCT CTCATTCAAT TCTGTGGAGG      1556

TCTGACATGA AGGCAATGCA TTCCTGGTTA CCACAGACTT CGCCCTTCCT TCCCAGACAC      1616

AAGAAGTAAT GGAGTGAATG TTGAGGGAGT CTCCTCTCAC TAAAGAAGAC TCTAGTGGGG      1676

CTGGATGTAC AGAACCTGCG TTGAAGGATC CCTAGGATGT TGGGAACACA GGGAGTGAAT      1736

TGAATTTAAA GAGGGCTAAA TTCACCTGTG TGGGTGCATT TGAGCAAATA AAAGATGGCG      1796

CCCAAAAAAA AAAAAAAAAA AAAAAAAAAA AAAA                                 1831
```

( 2 ) INFORMATION FOR SEQ ID NO:4:

( i ) SEQUENCE CHARACTERISTICS:
        ( A ) LENGTH: 320 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Lys Ala Asn Asn Thr Thr Thr Ser Ala Leu Trp Leu Gln Ile Thr
  1               5                  10                  15

Tyr Val Thr Met Glu Ala Ala Ile Gly Leu Cys Ala Val Val Gly Asn
             20                  25                  30

Met Leu Val Ile Trp Val Val Asn Leu Asn Arg Thr Leu Arg Thr Thr
         35                  40                  45

Thr Phe Tyr Phe Ile Val Ser Leu Ala Leu Ala Asp Ile Ala Val Gly
     50                  55                  60

Val Leu Val Ile Pro Leu Pro Ile Ala Val Ser Leu Glu Val Gln Met
 65              70                  75                      80

His Phe Tyr Ala Cys Leu Phe Met Ser Cys Val Leu Leu Val Phe Thr
                 85                  90                  95

His Ala Ser Ile Met Ser Leu Leu Ala Ile Ala Val Asp Arg Tyr Leu
            100                 105                 110

Arg Val Lys Leu Thr Val Arg Tyr Arg Thr Val Thr Thr Gln Arg Arg
        115                 120                 125

Ile Trp Leu Phe Leu Gly Leu Cys Trp Leu Val Ser Phe Leu Val Gly
    130                 135                 140

Leu Thr Pro Met Phe Gly Trp Asn Arg Lys Val Thr Leu Glu Leu Ser
145                 150                 155                 160

Gln Asn Ser Ser Thr Leu Ser Cys His Phe Arg Phe Val Val Gly Leu
                165                 170                 175

Asp Tyr Met Val Phe Phe Ser Phe Ile Thr Trp Ile Leu Ile Pro Leu
             180                 185                 190

Val Val Met Cys Ile Ile Tyr Leu Asp Ile Phe Tyr Ile Ile Arg Asn
         195                 200                 205

Lys Leu Ser Gln Asn Leu Thr Gly Phe Arg Glu Thr Arg Ala Phe Tyr
    210                 215                 220

Gly Arg Glu Phe Lys Thr Ala Lys Ser Leu Phe Leu Val Leu Phe Leu
225                 230                 235                 240

Phe Ala Leu Cys Trp Leu Pro Leu Ser Ile Ile Asn Phe Val Ser Tyr
                245                 250                 255

Phe Asn Val Lys Ile Pro Glu Ile Ala Met Cys Leu Gly Ile Leu Leu
             260                 265                 270

Ser His Ala Asn Ser Met Met Asn Pro Ile Val Tyr Ala Cys Lys Asn
         275                 280                 285

Lys Lys Val Gln Arg Asn His Phe Val Ile Leu Arg Ala Cys Arg Leu
    290                 295                 300

Cys Gln Thr Ser Asp Ser Leu Asp Ser Asn Leu Glu Gln Thr Thr Glu
305                 310                 315                 320
```

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TTTTCCTCCC CCCATTCAAA CCAGAT 26

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TTCCAGCTGA AGCTTCTC 18

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GGTGGAGCTG TTTTGAGA 18

A3 ADENOSINE RECEPTOR, DNA, AND USES

This invention was made with government support under MH45614 by the National Institute of Mental Health. The government has certain fights in the invention.

This application is a continuation of application Ser. No. 07/847,563, filed Mar. 3, 1992, now abandoned.

BACKGROUND OF THE INVENTION

1. Field of the Invention

This invention relates to adenosine receptors from mammalian species and the genes corresponding to such receptors. Specifically, the invention relates to the isolation, cloning and sequencing of a novel adenosine receptor gene, termed A3. The invention also relates to the construction of eukaryotic expression vectors capable of expressing this novel adenosine receptor in cultures of transformed eukaryotic cells, and the production of the A3 adenosine receptor in such cultures. The invention relates to the use of such cultures of transformed eukaryotic cells to produce the A3 adenosine receptor for the characterization of novel and useful drugs.

2. Background of the Invention

Adenosine modulates diverse physiological functions including induction of sedation, vasodilatation, suppression of cardiac rate and contractility, inhibition of platelet aggregability, stimulation of gluconeogenesis and inhibition of lipolysis (see, Stiles, 1986, Trends Pharmacol. Sci. 7: 486–490; Williams, 1987, Ann. Rev. Pharmacol. Toxicol. 27: 315–345; Ramkumar et al., 1988, Prog. Drug. Res. 32: 195–247). Based on biochemical and pharmacological criteria, two subtypes of adenosine receptor have been differentiated (termed A1 and A2), which inhibit and stimulate adenylate cyclase, respectively (Stiles, ibid.; Williams, ibid. ). Substantial progress has been made concerning the biochemical and pharmacological properties of these adenosine receptors such as ligand binding characteristics, glycosylation, and regulation. Besides its effects on adenylate cyclase, adenosine has been shown to open potassium channels, reduce flux through calcium channels, and inhibit or stimulate phosphoinositide turnover through receptor-mediated mechanisms (see, Fredholm & Dunwiddie, 1988, Trends Pharmacol. Sci. 9: 130–134; Sebastiao et al., 1990, Br. J. Pharmacol. 100: 55–62; Stiles, 1990, Clin. Res. 38: 10–18; Nakahata et al., 1991, J. Neurochem. 57: 963–969). In addition, the A1 adenosine receptor has been purified to homogeneity from rat and bovine brain (Nakata, 1989, J. Biol. Chem. 264: 16545–16551; Olah et al., 1990, Arch. Biochem. Biophys. 283: 440–446).

Recently, the cDNAs that encode the A1 and A2 adenosine receptors have been cloned (see, Libert et al., 1989, Science 244: 569–72; Maenhaet et al., 1990, Biochem. Biophys. Res. Commun. 173: 1169–1178; Libert et al., 1991, EMBO J. 10: 1677–1682; Mahan et al., 1991, Molecular Pharmacol. 40: 1–7; Reppert et al., 1991, Molec. Endo. 5: 1037–1048). Molecular cloning of A1 and A2 receptors revealed they both belong to the superfamily of G-protein coupled receptors. Physiological and pharmacological studies, however, have suggested the existence of additional adenosine receptors besides A1 and A2 (Linet al., 1991, J. Biol. Chem. 266: 14457–14463; Ribeiro & Sebastiao, 1986, Prog. Neurobiol. 26: 179–209; Oliveira et al., 1991, J. Neurochem. 57: 1165–1171; Ali et al., 1990, J. Biol. Chem..265: 745–753).

The present inventors have recently obtained a number of G-protein related clones using a polymerase chain reaction (PCR)-based random cloning strategy (Zhou et al., 1990, Nature 347: 76–80). The present invention comprises a novel adenosine receptor gene, termed A3, the nucleotide sequence of this gene and the deduced amino acid sequence of its cognate protein, a method for determining the tissue distribution of expression of the gene, and the determination of a number of pharmacological characteristics of the A3 receptor protein. A related nucleotide sequence has been reported recently (see Meyerhof et al., 1991, FEBS Lett. 284: 155–160).

DESCRIPTION OF THE DRAWINGS

FIGS. 1A to 1E illustrates the nucleotide (SEQ ID NO:3) and deduced amino acid sequence (SEQ ID NO:4) of R226 cDNA.

FIGS. 2A to 2C presents an amino acid sequence comparison between the A 1, A2 and A3 (SEQ ID NO:4) adenosine receptor proteins.

FIG. 3 illustrates a Scatchard plot of radioligand binding assays for the A3 adenosine receptor performed with the adenosine radioligand [$^{125}$I]APEA and membrane preparations from stably transfected CHO cells.

SUMMARY OF THE INVENTION

Figure 4A:
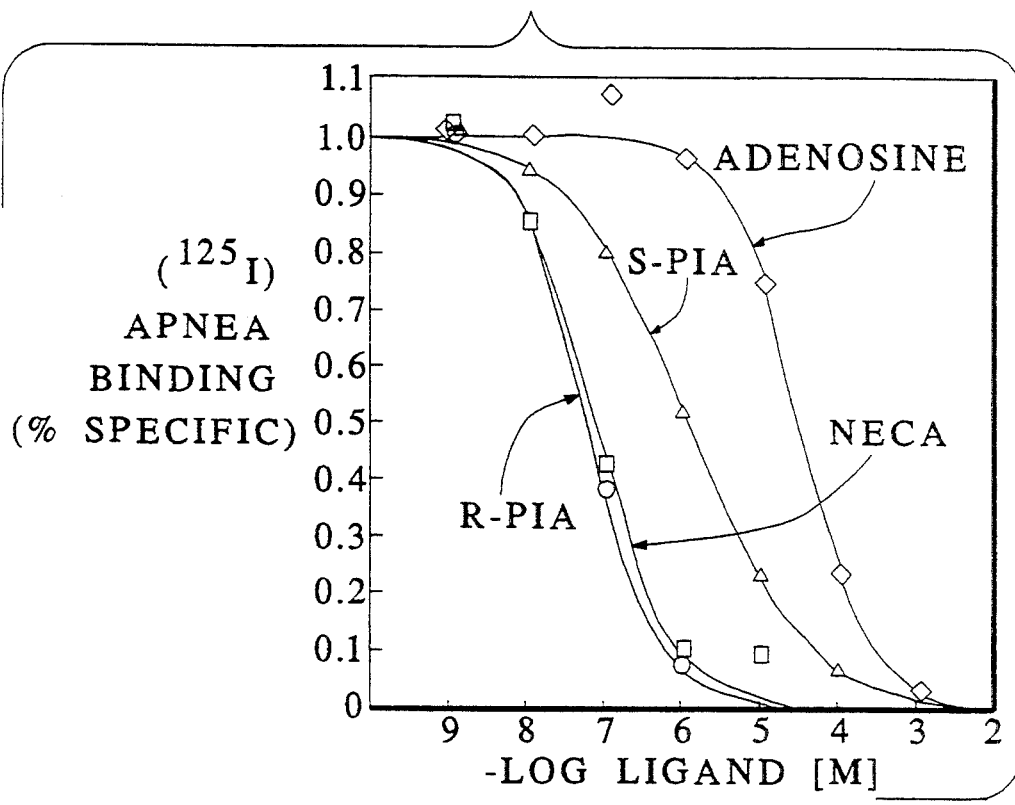
FIGS. 4A and 4B illustrates competitive binding assays using stably transfected CHO cell membrane preparations. Panel A shows competition between 0.5 nM [$^{125}$I]APNEA and varying concentrations of adenosine receptor agonists. Panel B shows competition between 0.5 nM [$^{125}$I]APNEA and varying concentrations of Gpp(NH)p and the P2 purinergic receptor agonists ATP and ADP.

The present invention relates to the cloning, expression and functional characterization of a novel adenosine receptor. The invention comprises the nucleotide sequence of the gene encoding this novel adenosine receptor and the deduced amino acid sequence of its cognate protein, as well as its tissue distribution and its pharmacological characterization.

In particular, the present invention is directed toward the isolation, characterization and pharmacological use of the rat A3 adenosine receptor, the gene corresponding to this receptor, a recombinant eukaryotic expression construct capable of expressing the rat A3 adenosine receptor in cultures of transformed eukaryotic cells and such cultures of transformed eukaryotic cells that synthesize the rat A3 adenosine receptor.

It is an object of the invention to provide a nucleotide sequence encoding a mammalian adenosine receptor. In a preferred embodiment of the invention, the nucleotide sequence encodes the rat adenosine receptor A3.

Further, it is an object of the invention to provide a nucleotide sequence that encodes a mammalian adenosine receptor with novel and distinct pharmacological properties. It is specifically an object of the invention to provide a nucleotide sequence encoding a mammalian adenosine receptor having the particular drug dissociation properties of the rat adenosine receptor A3. In particular, the mammalian adenosine receptor encoded by the nucleotide sequence of the present invention shows saturable and high affinity binding of the adenosine receptor agonist APNEA. The A3 adenosine receptor embodied in the present invention displays the adenosine agonist binding profile presented in Table I. The rat A3 adenosine receptor embodied in the present invention displays the following pharmacological profile of inhibition of [$^{125}$I]APNEA binding in a binding assay: R-PIA=NECA>S-PIA>adenosine>ATP-=ADP.

The present invention includes a nucleotide sequence encoding a rat adenosine receptor derived from a cDNA molecule isolated from a cDNA library constructed with RNA from rat brain (SEQ ID NO:3). In this embodiment of the invention, the nucleotide sequence includes 1831 nucleotides of the rat A3 adenosine receptor gene comprising 960 nucleotides of coding sequence, 316 nucleotides of 5' untranslated sequence and 555 nucleotides of 3' untranslated sequence.

The invention also includes a nucleotide sequence derived from rat genomic DNA. In this embodiment of the invention, the nucleotide sequence includes 2.8 kilobases (kb) of rat genomic DNA comprising the novel adenosine receptor A3. This embodiment includes the sequences present in the cDNA embodiment, as well as intervening sequences and flanking genomic sequences.

The invention includes a nucleotide sequence of a rat A3 adenosine receptor (SEQ ID NO:3), and includes allelic variations of this nucleotide sequence and the corresponding A3 receptor molecule, either naturally occurring or the product of in vitro chemical or genetic modification, having essentially the same nucleotide sequence as the nucleotide sequence of the rat A3 receptor disclosed herein, wherein the resulting A3 receptor molecule has substantially the same drug dissociation properties of the A3 receptor molecule corresponding to the nucleotide sequence described herein. The term "substantially homologous to" as used in this invention encompasses such allelic variability as described in this paragraph.

The invention also includes a predicted amino acid sequence for the rat A3 adenosine receptor deduced from the nucleotide sequence comprising the complete coding sequence of the A3 adenosine receptor gene (SEQ ID NO:4).

In another aspect, the invention comprises a homogeneous composition of a 37 kilodalton adenosine receptor A3 or derivative thereof, wherein the amino acid sequence of the adenosine receptor or derivative thereof comprises a sequence shown in FIGS. 2A to 2C (SEQ ID NO: 4).

This invention provides both nucleotide and amino acid probes derived from these sequences. The invention includes probes isolated from either the cDNA or genomic DNA clones, as well as probes made synthetically with the sequence information derived therefrom. The invention specifically includes but is not limited to oligonucleotide, nick-translated, random primed, or in vitro amplified probes made using the cDNA or genomic clone embodying the invention, and oligonucleotide and other synthetic probes synthesized chemically using the nucleotide sequence information of the cDNA or genomic clone embodiments of the invention.

It is a further object of this invention to provide sequences of the rat A3 adenosine receptor for use as probes to determine the pattern, amount and extent of expression of this receptor in various tissues of mammals, including humans. It is also an object of the present invention to provide probes derived from the sequences of the rat A3 adenosine receptor to be used for the detection and diagnosis of genetic diseases. It is an object of this invention to provide probes derived from the sequences of the rat A3 adenosine receptor to be used for the detection of novel related receptor genes, including the human homologue of the rat A3 adenosine receptor gene described herein.

The present invention also includes synthetic peptides made using the nucleotide sequence information comprising the cDNA or genomic clone embodiments of the invention. The invention includes either naturally occurring or synthetic peptides which may be used as antigens for the production of A3 adenosine receptor-specific antibodies, or used for competitors of the A3 receptor molecule for drug binding, or to be used for the production of inhibitors of the binding of adenosine, adenosine agonists or antagonists or analogues thereof to the A3 adenosine receptor molecule.

In addition, this invention includes a cloning vector comprising the rat A3 adenosine receptor and sequences that mediate the replication and selected growth of microorganisms that carry this vector.

The present invention provides a recombinant expression construct comprising the nucleotide sequence of the rat A3 adenosine receptor and sequences sufficient to direct the synthesis of rat A3 adenosine receptor in cultures of transformed eukaryotic cells. In a preferred embodiment, the recombinant expression construct is comprised of plasmid sequences derived from the plasmid pBC12BI and cDNA or genomic DNA of the rat A3 adenosine receptor gene. In an additional preferred embodiment, the recombinant expression construct is comprised of sequences derived from the expression vector Rc-RSV and cDNA or genomic DNA of the rat A3 adenosine receptor gene. This invention includes a recombinant expression construct comprising essentially the nucleotide sequences of genomic or cDNA clones of the rat A3 adenosine receptor in an embodiment that provides for their expression in cultures of transformed eukaryotic cells.

It is also an object of this invention to provide cultures of transformed eukaryotic cells that have been transformed with such a recombinant expression construct and that synthesize rat A3 adenosine receptor protein. In a preferred embodiment, the invention provides monkey COS cells that synthesize rat A3 adenosine receptor protein. In an additional preferred embodiment, the invention provides Chinese hamster ovary (CHO) cells that synthesize rat A3 adenosine receptor protein.

The present invention also includes protein preparations of the rat A3 adenosine receptor, and preparations of membranes containing the rat A3 adenosine receptor, derived from cultures of transformed eukaryotic cells. In a preferred embodiment, cell membranes containing rat A3 adenosine receptor protein are isolated from COS-7 cell cultures transformed with a recombinant expression construct that directs the synthesis of rat A3 adenosine receptor. In another preferred embodiment, cell membranes containing rat A3 adenosine receptor protein are isolated from CHO cell cultures transformed with a recombinant expression construct that directs the synthesis of rat A3 adenosine receptor.

It also an object of this invention to provide the rat A3 adenosine receptor for use in the in vitro screening of novel adenosine agonist and antagonist compounds. In a preferred embodiment, membrane preparations containing the rat A3 adenosine receptor, derived from cultures of transformed eukaryotic cells, are used to determine the drug dissociation properties of various novel adenosine agonist and antagonist compounds in vitro. These properties are then used to characterize such novel compounds by comparison to the binding properties of known adenosine agonists and antagonists.

The present invention will also be useful for the in vivo detection of adenosine or adenosine analogues, known or unknown, either naturally occurring or as the embodiments of a drug.

It is an object of the present invention to provide a method for the quantitative detection of adenosine or adenosine analogues, either naturally occurring or as the embodiments of a drug. It is an additional object of the invention to provide a method to detect adenosine or an adenosine analog in blood, saliva, semen, cerebrospinal fluid, plasma, lymph, or any other bodily fluid.

The invention also provides a method for detection of A3 adenosine receptor expression is blood or tissue samples, comprising the steps of:
(a) isolating cellular RNA from the blood or tissue samples;
(b) converting the RNA to cDNA;
(c) providing a mixture comprising a DNA polymerase, deoxynucleotide triphosphates, the cDNA, and a pair of primers comprising DNA sequences substantially equal to

5'-TTCCAGCTGAAGCTTCTC-3'     (SEQ ID NO:6)

5'-GGTGGAGCTGTTTTGAGA-3'     (SEQ ID NO:7)

(d) amplifying the cDNA by subjecting the mixture to alternating cycles of temperatures which allow denaturation, annealing and DNA synthesis; and
(e) determining whether a product is obtained from amplifying the cDNA.

Specific preferred embodiments of the present invention will become evident from the following more detailed description of certain preferred embodiments and the claims.

DETAILED DESCRIPTION OF THE PREFERRED EMBODIMENTS

The term "A3 adenosine receptor" as used herein refers to proteins substantially homologous to, and having substantially the same biological activity as, the protein coded for by the nucleotide sequence depicted in FIGS. 1A to 1E (SEQ ID NO:3). This definition is intended to encompass natural allelic variations in the A3 adenosine receptor sequence. Cloned genes of the present invention may code for A3 adenosine receptors of any species of origin, including, for example, mouse, rat, rabbit, cat, and human, but preferably code for receptors of mammalian, most preferably rat and human, origin.

The production of proteins such as the A3 adenosine receptor from cloned genes by genetic engineering is well known. See, e.g., U.S. Pat. No. 4,761,371 to Bell et al. at Col. 6 line 3 to Col. 9 line 65. (The disclosure of all U.S. patent references cited herein is to be incorporated herein by reference.) The discussion which follows is accordingly intended as an overview of this field, and is not intended to reflect the full state of the art.

DNA which encodes the A3 adenosine receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the A3 adenosine receptor gene sequence information provided herein. Probes may be labeled with a detectable group such as a fluorescent group, a radioactive atom or a chemiluminescent group in accordance with know procedures and used in conventional hybridization assays, as described in greater detail in the Examples below. In the alternative, A3 adenosine receptor gene sequences may be obtained by use of the polymerase chain reaction (PCR) procedure, with the PCR oligonucleotide primers being produced from the A3 adenosine receptor gene sequence provided herein. See U.S. Pat. Nos. 4,683,195 to Mullis et al. and 4,683,202 to Mullis.

The A3 adenosine receptor may be synthesized in host cells transformed with vectors containing DNA encoding the A3 adenosine receptor. A vector is a replicable DNA construct. Vectors are used herein either to amplify DNA encoding the A3 adenosine receptor and/or to express DNA which encodes the A3 adenosine receptor. A recombinant expression construct is a replicable DNA construct in which a DNA sequence encoding the A3 adenosine receptor is operably linked to suitable control sequences capable of effecting the expression of the A3 adenosine receptor in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the A3 adenosine receptor recombinant expression constructs made using recombinant DNA techniques. Transformed host cells ordinarily express the A3 receptor, but host cells transformed for purposes of cloning or amplifying the A3 receptor DNA need not express the receptor. When expressed, the A3 receptor will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leaders sequences, contiguous and in the same translational reading frame.

Cultures of cells derived from multicellular organisms are a desirable host for recombinant A3 adenosine receptor synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice sites (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, adenovirus 2, and simian virus 40 (SV40). See, e.g., U.S. Pat. No. 4,599,308. The early and late promoters of SV40 are useful because both are obtained easily from the virus as a fragment which also contains the SV40 viral origin of replication. See Fiers et al., Nature 273, 113 (1978). Further, the human genomic A3 receptor promoter, control and/or signal sequences, may also be used, provided such control sequences are compatible with the host cell chosen.

An origin of replication may be provided either by construction of the vector to include an exogenous origin, such as may be derived from SV40 or other viral source (e.g., polyoma, adenovirus, VSV, or MPV), or may be provided by the host cell chromosomal replication mechanism. If the vector is integrated into the host cell chromosome, the latter may be sufficient.

A3 adenosine receptors made from cloned genes in accordance with the present invention may be used for screening compounds for A3 adenosine receptor activity, or for determining the amount of an adenosine agonist or antagonist drug in a solution (e.g., blood plasma or serum). For example, host cells may be transformed with a vector of the present invention, A3 adenosine receptors expressed in that host, the cells lysed, and the membranes from those cells used to screen compounds for A3 adenosine receptor binding activity. Competitive binding assays in which such procedures may be carried out are well known, as illustrated by the Examples below. By selection of host cells which do not ordinarily express adenosine receptors, pure preparations of membranes containing A3 adenosine receptors can be obtained. Further, A3 adenosine receptor agonist and antagonists can be identified by transforming host cells with vectors of the present invention. Membranes obtained from such cells can be used in binding studies wherein the drug dissociation activity is monitored. Such cells must contain A3 protein in the plasma and other cell membranes. Procedures for carrying out assays such as these are also described in greater detail in the Examples which follow.

The recombinant expression constructs of the present invention are useful in molecular biology to transform cells which do not ordinarily express the A3 adenosine receptor to thereafter express this receptor. Such cells are useful as intermediates for making cell membrane preparations useful for receptor binding assays, which are in turn useful for drug screening. Further, genes and vectors comprising the recombinant expression construct of the present invention are useful in gene therapy. For such purposes, retroviral vectors as described in U.S. Pat. No. 4,650,764 to Temin & Watanabe or U.S. Pat. No. 4,861,719 to Miller may be employed. Cloned genes of the present invention, or fragments thereof, may also be used in gene therapy carried out homologous recombination or site-directed mutagenesis. See generally Thomas & Capecchi, 1987, Cell 51: 503–512; Bertling, 1987, Bioscience Reports 7: 107–112; Smithies et al., 1985, Nature 317: 230–234.

Cloned genes of the present invention, and oligonucleotides derived therefrom, are useful for screening for restriction fragment length polymorphism (RFLP) associated with certain genetic disorders.

Oligonucleotides of the present invention are useful as diagnostic tools for probing A3-receptor gene expression in tissues. For example, tissues can be probed in situ with oligonucleotide probes carrying detectable groups by conventional autoradiography techniques, as explained in greater detail in the Examples below, to investigate native expression of this receptor or pathological conditions relating thereto. Further, chromosomes can be probed to investigate the presence or absence of the A3 adenosine receptor gene, and potential pathological conditions related thereto, as also illustrated by the Examples below.

In the practice of the method of the invention for detecting A3 adenosine receptor gene expression, the term "substantially equal to" with reference to the primer sequences therein will be understood as used with this invention to include primers that differ in sequence to a limited degree; this degree of sequence divergence is tightly controlled by the reaction conditions provided in the specification, which results in the specific production of a 531 basepair DNA fragment derived from A3 adenosine receptor mRNA. It is well-known in the art that the specificity of PCR amplification of cDNA sequences depends on the complexity of the primer sequences and the annealing temperature conditions used for amplification [see, for example, Saiki, *The Design and Optimization of PCR*, in *PCR Technology*, Erlich (ed.), Stockton Press, New York, 1989, pp. 7–16]. It is also well-known, however, that some variation in primer sequence can be tolerated and still produce a valid result, and that production of such variation in primer sequence does not entail undue experimentation [see, for example, Chumakov et al., 1991, Proc. Natl. Acad. Sci. USA 88: 199–203]. In fact, such variations have been used experimentally to introduce mutations in certain gene sequences [Higuchi, *Using PCR to Engineer DNA*, in *PCR Technology*, Erlich (ed.), Stockton Press, New York, 1989, pp. 61–70]. The term "substantially comprising" as used herein is therefore necessary to define the proper metes and bounds of the invention, and to prevent a competitor from avoiding infringement simply by making a superficial change in primer sequence.

The Examples which follow are illustrative of specific embodiments of the invention, and various uses thereof. They are set forth for explanatory purposes only, and are not to be taken as limiting the invention.

EXAMPLE 1

Isolation of an Adenosine Receptor Probe by Random PCR Amplification of Rat Striatal cDNA Using Degenerate Oligonucleotide Primers In order to clone novel G-protein coupled receptors, rat striatal cDNA was used as template for a polymerase chain reaction (PCR)-based random cloning experiment. PCR was performed using a pair of degenerate oligonucleotide primers corresponding to the putative third and sixth transmembrane regions of G-protein coupled receptors (Libert et al., 1989, Science 2.44: 569–72; Zhou et al., 1990, Nature 347: 76–80). The PCR products obtained in this experiment were characterized by nucleotide sequencing. Five novel sequences representing novel G-protein-coupled receptors were identified. One of these fragments, PCR226, exhibited pronounced sequence homology with the two previously cloned adenosine receptors [discussed supra in the Background of the Invention section and references therein].

PCR amplification was performed as follows. Total RNA was isolated from rat striatal tissue by the guanidinium thiocyanate method (Chirgwin et al., 1979, Biochemistry 18: 5294–5299). PolyA+ mRNA was purified by oligo-dT cellulose affinity chromatography by the method of Aviv and Leder (1972, Proc. Natl. Acd. Sci. USA 69: 1408–1413). Double-stranded cDNA was synthesized from polyA+ RNA with murine reverse transcriptase (BRL, Gaithersburg, Md.) by oligoodT priming [Maniatis et al., *Molecular Cloning: A Laboratory Manual*, (Cold Spring Harbor Laboratory Press, Cold Spring Harbor, N.Y.), 1990]. The striatal cDNA mixture was then subjected to 30 cycles of PCR amplification using 20 picomoles of degenerate oligonucleotide primers having the following sequence:

Primer III (sense):

GAGTCGACCTGTG(C/T)G(C/T)(C/G)AT(C/T)(A/G)CIIT(G/T)GAC(C/A)G(C/G)TAC    (SEQ ID NO: 1)

and

Primer VI (antisense):

CAGAATTCAG(T/A)AGGGCAICCAGCAGAI(G/C)(G/A)(T/G)GAA    (SEQ ID NO: 2)

in 20μl of a solution containing 50 mM Tris-HCl (pH 8.3), 2.5 mM MgCl$_2$, 0.01% gelatin, 200 μM each dNTP, and 2.5 units of Taq polymerase (Zhou, ibid.; Saiki et al., 1988, Science 239: 487–491 ). These primers were commercially synthesized by Research Genetics Inc. (Huntsville, Ala.). Each PCR amplification cycle consisted of incubations at 95° C. for 1 min (denaturation), 42° C. for 1 min (annealing), and 72° C. for 1.5 min (extension).

Amplified products of the PCR reaction were extracted with phenol/chloroform and precipitated with ethanol. After digestion with EcoRI and SalI, the PCR products were separated on a 1.2% agarose gel. A slice of this gel, corresponding to PCR products of 400–750 basepairs (dp) in size, was cut out and purified using the Prep-A-Gene kit (Bio-Rad, Richmond, Calif.) and subcloned into M 13mp18 and M 13mp19 (Boehringer Mannheim, Indianapolis, Ind.).

A total of fifty of such M13 clones containing inserts were sequenced using Sequenase (U.S. Biochemical Corp., Cleveland, Ohio) by the dideoxynucleotide chain termination method (Sanger et al., 1977, Proc. Natl. Acad. Sci. USA 74: 5463–5467). One PCR fragment (named PCR226) was identified that had sequence homology to known adenosine receptors.

EXAMPLE 2

Isolation and Sequence Analysis of Adenosine Receptor A3 cDNA

The probe isolated in Example 1 was used to screen a rat brain cDNA library in order to isolate a full-length cDNA corresponding to the cloned probe. One clone was isolated from a library of one million clones constructed and screened as described below. This clone contained an insert of 1.9 kilobases (kb), and its complete nucleotide sequence was determined (as shown in FIGS. 1A to 1E; SEQ ID NO:3).

The PCR226 probe was labeled by the random-priming method (Stratagene PrimeIt, #300387, LaJolla, Calif.) and used to screen two libraries by plaque hybridization (Maniatis et al., ibid.). The libraries screened were: 1. a library of $10^6$ clones containing rat brain cDNA inserts constructed in lambda-gtl1; and 2.50,000 clones from a rat genomic library carried in lambda-DASH (Stratagene). Library screening was performed using techniques well-known in the art as described in Bunzow et al. (1988, Nature 336: 783–787). One cDNA clone was identified (R226) and its 1.9 kb cDNA insert was isolated and subcloned into pGemBlue (Stratagene); the resulting plasmid was called pGem226. Two identical positive genomic phage were also plaque purified and then characterized by Southern blot hybridization. A 2.8 kb BglII fragment from the genomic phage DNA that hybridized to the PCR226 probe was subcloned into pBluescript (Stratagene) by shot-gun cloning and called pBS226. Small fragments from pGem226 and pBS226 were subcloned into M13 vectors and sequenced as described above. The sequencing strategy used employed synthetic oligonucleotides primers derived from the deduced sequence to facilitate sequencing. Nucleotide sequence analysis and homology comparisons were done on the SUN/UNIX computer system with software provided by Intelligenetics Inc. (Mountain View, Calif.).

The nucleotide sequence of R226 (the cDNA clone isolated as described above) is shown in FIGS. 1A to 1E (SEQ ID NO:3). Numbering starts with the first methionine of the A3 open reading frame (ORF). Putative transmembrane domains are boxed. A very pyrimidine-rich (94% T/C) sequence in the 3' untranslated region is underlined. A putative polyadenylation site has two lines below it. The potential N-glycosylation sites are indicated by star (*). The arrow indicates the position of a splice site. The RNA destability consensus sequence signals (AUUUA; Shaw & Kamen, 1986, Cell 46: 659–667) are in boldface type. The potential protein kinase c phoshorylation sites and casein kinase II phosphorylation site are indicated by # and $, respectively.

The longest open reading frame of this cDNA encodes a predicted protein product of 320 amino acids with a calculated molecular weight of 37 kD. A Kozak consensus sequence (A/GNNATGA; 1984, Nucl. Acids Res. 12: 857–872) is found around the presumed translation start codon. Actual utilization of this start codon is also indicated by the presence of an in-frame stop codon found 9 base pairs 5' of this initiation codon. The 3' untranslated region contains one polyadenylation site (AAUAAA) and two mRNA instability signals (AUUUA). A stretch of over 120 bp of pyrimidine-rich sequence was also found in the 3' untranslated region. Although this type of nucleotide repeat is often found in intron and flanking regions of vertebrate genes, they are rarely found within transcribed mRNA (Rogers, 1983, Nature 305: 101–102). Although the functional significance of this sequence is unknown, similar repetitive sequences has also been found in the 5' and 3' untranslated regions of substance P receptor cDNA (Yokota et al., 1989, J. Biol. Chem. 264: 17649–17652).

The deduced amino acid sequence of the protein encoded by R226 is shown in FIGS. 2A to 2C (SEQ ID NO:4). Hydrophobicity analysis (Kyte & Doolittle, 1982, J. Mol. Biol. 157: 105–132) of the deduced amino acid sequence showed that the protein contains seven hydrophobic stretches of 21 to 26 amino acids apiece. Sequence comparison analysis between the A1, A2 and A3 adenosine receptors is presented in FIGS. 2A to 2C. The putative transmembrane domains are boxed and bracketed and labelled by Roman numerals. Shaded amino acid residues are conserved in all three adenosine receptors. This analysis revealed that R226 is significantly homologous to known adenosine receptors. Within putative transmembrane domains, the amino acid sequence of R226 is 58% identical to the A1 receptor (clone RDC7) and 57% identical to the A2 receptor (clone RDC8). These three receptors share 46 % identity between the amino acids comprising the putative transmembrane domains. These percentages of sequence identity are similar to what has been found between different members of the adrenergic and dopaminergic receptor subfamilies (O'Dowd et al., 1989, Ann. Rev. Neurosci. 12: 67–83; Civelli et al., 1991, Eur. J. Pharmacol. Molec. Pharmacol. 207: 277–286). The high degree of sequence similarity found among A1, A2 and R226 suggests that they belong to the same subclass of G-protein coupled receptor.

Additional sequence similarity was found among these sequences at the putative N-glycosylation site in the second extracellular loop (shown in FIGS. 1A to 1E). Two potential N-glycosylation sites (Asn-4 and Asn-5) were found in the N-terminus of R226, in contrast to the A1 and A2 adenosine receptors (which lack N-glycosylation site in their N-termini). A search for potential phosphorylation sites revealed the presence of three protein kinase C sites (consensus sequence S/T-X-R/K; Kishimoto et al., 1985, J. Biol. Chem. 260: 12492–12499). On the other hand, no consensus sequences for protein kinase A phosphorylation have been found (R/K-R/K-X-S/T; Dohlman et al., 1987, J. Biochem. 26: 2657–2664). Interestingly, a potential casein kinase II phosphorylation site (S/T-X-X-E/D; Edelman et al., 1987, Ann. Rev. Biochem. 56: 567–613) was found in the short C-tail of R226. These potential phosphorylation sites could be involved in receptor regulation (Olah et al., 1990, Arch. Biochem. Biophys. 283: 440–446).

Isolation and partial characterization of rat genomic clones of R226 revealed the existence of at least one intron having donor/acceptor splice sites with the following sequence:

TTTTCCTCCCCCCATTCAAACCAG/AT    (SEQ ID NO: 5)

This splice site is located just outside the third transmembrane domain of R226, and there is also a stretch of pyrimidines immediately preceding the splice site (Mount, 1982, Nucl. Acids Res. 10: 459–471). Comparison with the genomic arrangement of splice sites from other members of the G-protein coupled receptor family that contain introns suggests that this splice site is conserved (Hershey et al., 1991, J. Biol. Chem. 266: 4366–4374). The mRNA sequence of R226 found 3' to this splice site is contained in a single exon, and the intron preceding this exon is at least 2 kb long.

On the basis the foregoing sequence comparison, we conclude that R226 belongs to the superfamily of G protein-coupled receptors and in particular to the adenosine receptor family. Sequence divergence from the known A1 and A2 receptors indicates that R226 represents a novel adenosine receptor, which we have termed A3.

EXAMPLE 3

Construction of A3 Expression Plasmids and DNA Transfection

In order to characterize the A3 adenosine receptor biochemically and pharmacologically, R226 was cloned into a mammalian expression vector, this vector transfected into COS-7 and CHO cells, and cell lines generated that express the A3 receptor at the cell surface. Such cells and membranes isolated from such cells were used for the biochemical and pharmacological characterization experiments that are described in Examples 4 & 5.

The entire coding region of the A3 cDNA insert from R226 was excised from pGem226 and subcloned into either the HindIII/XbaI sites of an RC-RSV expression vector (Invitrogene, San Diego, Calif.) or the HindIII/SmaI sites of pBC12BI (Cullen, 1987, Meth. Enzym. 152: 684–704). The resulting plasmids were called Rc-RSV226 and pBC226 respectively. For transient expression in COS-7 cells, pBC226 plasmid DNA was prepared in large-scale through one cycle of CsCl gradient ultracentrifugation and 45 μg pBC226 DNA were transfected into each 150mm dish of COS-7 cells according to the method of Chen and Okayama (1987, Molec. Cell Biol. 7: 2745–2752). For stable expression in CHO cells, 1 μg Rc-RSV226 plasmid DNA isolated from a small-scale preparation was purified using the Prep-A-Gene kit (Bio-Rad) and transfected into CHO cells by the CaPO4 method (Graham and van der Eb, 1973, Virol. 52: 456-463). After transfection, cells were cultured in DMEM (COS-7 cells) or F-12 (CHO cells) media supplemented with 10% fetal calf serum in a 3% $CO_2$ atmosphere at 37° C. For stable transfection, selection was performed with neomycin (G418; SOURCE) at a concentration of 700 μg/ml; selection was started 72 hr after transfection and continued for 3 weeks. Cell colonies were screened for expression of the A3 adenosine receptor from the R226 expression vectors described herein by Northern blot hybridization of total cellular RNA with random-primed PCR226 probe (Maniatis et al., ibid.).

EXAMPLE 4

Biochemical and Pharmacological Characterization of the A3 Adenosine Receptor

The A3 adenosine receptor was characterized using cells and membranes from cells either transiently (COS-7) or stably (CHO) expressing the receptor after transfection with expression vector constructs as described in Example 3. The results of these experiments are shown in FIGS. 3-7.

Cell membranes were prepared as follows. COS-7 cells (transient expressors) were harvested 48 hrs after transfection, whereas CHO cells (stable expressors) were grown to confluence in 150 mm plates. Cells were washed twice with ice-cold HOB buffer [15 mM Tris-HCl (pH 7.4), 5 mM $MgCl_2$, 1 mM EDTA] and scraped off plates with a rubber policeman. Cells were then collected by centrifugation at 1,200 rpm (xx g), resuspended in HOB buffer, transferred to a Dounce homogenizer on ice, and homogenized for 20 sec with a Cor-Targe homogenizer (Eberbach Inc., Ann Arbor, Mich.) at the #3 speed setting. The homogenate was then centrifuged at 2,000 rpm (xx g) for 10 min at 4° C. The supernatant was saved and the pellet resuspended in HOB buffer and subjected to a second round of homogenation. The second homogenate was centrifuged at 2000 rpm (xx g) for 10 min and the pellet was discarded. Supernatants were pooled and centrifuged at 34,000 rpm (xx g) for 45 min. These crude membrane pellets were resuspended in TEM buffer [50 mM Tris-HCl (pH 7.4), 5 mM $MgCl_2$, 1 mM EDTA]. Adenosine deaminase (Sigma, St Louis, Mo.) was added to the membrane suspensions to a concentration of 2 Units/ml and incubated at 37° C. for 30 min. The membrane suspension was subsequently recentrifuged at 34,000 rpm (xx g) for 45 min. The resulting pellet was resuspended in TEM buffer at a protein concentration of about 1 mg/ml and stored in small aliquots at −70° C. The protein concentration was measured according to the method of Lowry et al. (1954, J. Biol. Chem. 207: 1-XXX) using bovine serum albumin as a standard.

Radioligand binding assays were carried out in duplicate in 500 μl of a solution containing (at final concentrations) 50 mM Tris-HCl (pH 7.4), 5 mM $MgCl_2$, 1 mM EDTA, 0.025 % ascorbic acid, radioligands, and appropriate drugs. Radioligands tested include: [$H^3$]-labeled N-ethyladenosine-5′-uronic acid ([$^3H$]NECA), [$^3H$]-labeled 1,3-dipropyl-8-cyclopentylxanthine ([$^3H$]DPCPX), [$^{125}I$]-labeled $N^6$-2-(4-amino-3-iodo-phenyl) ethyladenosine ([$^{125}I$]APNEA)], [$^3H$]-labeled WHAT IS XAC?? ([aH]XAC), [$^3H$]-labeled 2-[4-(2-[(4-aminophenyl)methylcarbobylamino]ethylaminocarbonyl)ethyl]phenyl]ethylamino-5′-N-ethylcarboxamidoadenosine ([$^3H$]PAPA-APEC), and [$^3H$]-labeled [2-(4-(2-carboxyethyl)phenylethyamino)5′-N-ethylcarboxamidoadenosine ([$^3H$]CGS21680). Receptor binding was initiated by the addition of membrane preparations in an amount equivalent to 20-100 μg protein, and carried out at 37° C. for 1 hr. Nonspecific binding was determined in the presence of 10 μM R-$N^6$-phenyl-2-propyladenosine (R-PIA). After incubation, samples were filtered through glass fiber filters (Schleicher and Schuell #32) and washed three times with 4 ml ice-cold 10 mM TrisoHCl (pH 7.4). Radioactivity retained on the filters were counted using a Beckman LS6800 scintillation counter (Beckman Instruments, Palo Alto, Calif.). Inhibition curves were best fitted by assuming the existence of one or two classes of ligand binding site. The 50% inhibition concentration (IC$_{50}$) calculated from the curves were converted to $K_i$ values as described in Cheng & Prusoff (1973, Biochem. Pharmacol. 22: 3099-3108). A LIGAND computer program was used for data analysis and curve fitting (Munson & Rodband, 1980, Anal. Biochem. 107: 220-225).

Initial binding assays of transiently transfected COS-7 cell membrane preparations performed with the nonselective adenosine radioligand [$^3H$]NECA showed saturable and high affinity radioligand binding. To further characterize the A3 receptor binding of A1 and A2 specific ligands (and to avoid the low level of endogenous A2 receptor in COS-7 cells; Maenhaet et al., 1990, ibid.), we analyzed adenosine receptor ligand binding in stably expressing CHO cells, which do not express endogenous adenosine receptors as judged by [$^3H$]NECA binding analysis. Using membranes from these stably transformed CHO cells, A3 binding of a variety of adenosine receptor ligands was tested. Such ligands include: 1. the A1 selective agonists APNEA ($^{125}I$-labeled), DPCPX ($^3H$-labeled) and XAC ($^3H$-labeled); and 2. the A2 selective agonists CGS21680 (3H-labeled) and PAPA-APEC ($^{125}I$-labeled). The only adenosine receptor ligand to show specific, high affinity binding to the A3 receptor was the A1 selective agonist [$^{125}I$]APNEA. Scatchard plot analysis (presented in FIG. 3) showed A3 receptor APNEA binding that was saturable (225 fmol/mg) and high affinity ($K_d$=15.5 ±2.4 nM). This affinity is about ten-fold lower than that found for other, well-characterized A1 receptors (see, Stiles et al., 1985, J. Biol. Chem. 260: 10806-10811).

The A3 receptor was then characterized using competition assays between [$^{125}I$]APNEA A3 receptor binding versus a series of other adenosine receptor ligands. Labeled APNEA was present in these assays at 0.5 nM; unlabled competitors were present at varying concentrations as shown in FIG. 4A. IC$_{50}$ values for each competitive ligand were determined and are presented graphically in FIG. 4A and shown in Table I as follows:

TABLE I

| DRUG | IC$_{50}$ |
| --- | --- |
| R-PIA | 63 ± 19 nM |
| NECA | 74 ± 23 nM |
| S-PIA | 1140 ± 490 nM |
| Adenosine | 30 ± 4 μM |

A constant feature of all previously known adenosine receptors is that methylxanthines are receptor antagonists [CITE]. Accordingly, the methylxanthines IBMX [WHAT IS THIS?], PDCPX and XAC were tested for their ability to compete with [$^{125}I$]-labeled APNEA for A3 receptor binding. In contrast to all other known adenosine receptors, none of the methylxanthines tested were capable of competing with labeled APNEA for A3 adenosine receptor binding even when present at 100 μM concentrations.

Figure 4B:
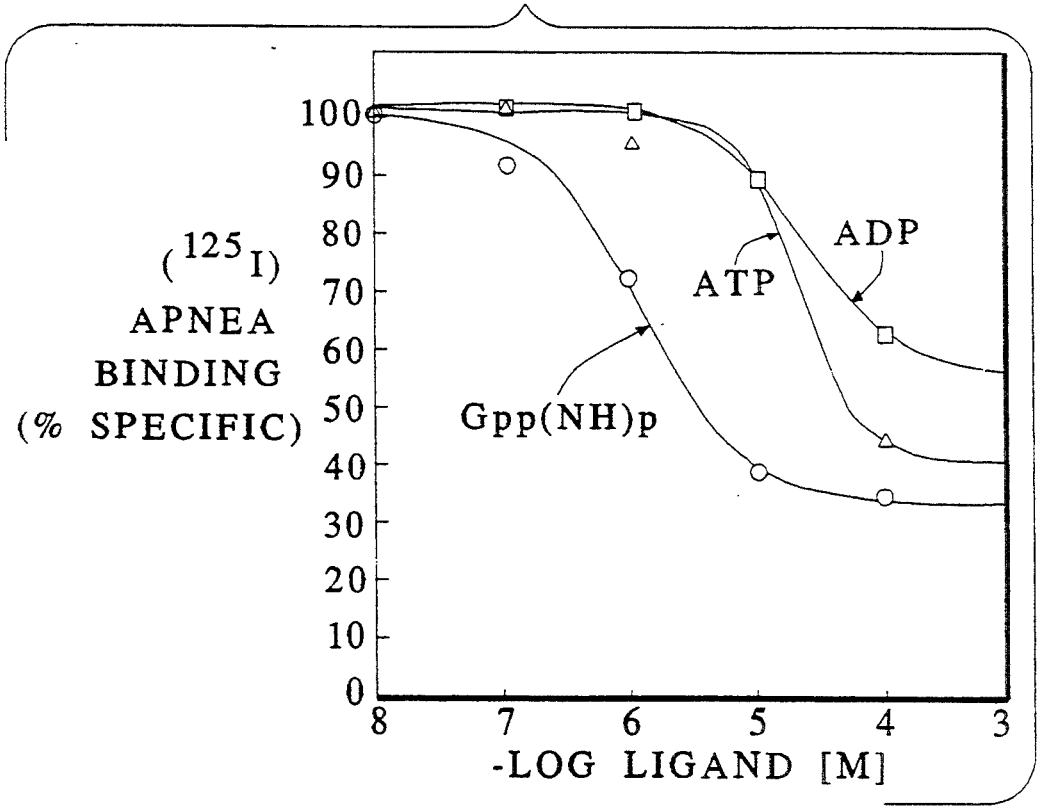

Since the pharmacology and ligand affinities exhibited by the A3 receptor are not consistent with either the A1- or A2-type adenosine receptor known in the prior art, the possibility that A3 was a P2 purinergic receptor or other nucleoside/nucleotide binding protein (Boeynauers, 1990, Trends Pharmacol. Sci. 11: 34-37) was tested. As shown in FIG. 4B, at concentrations of 100 μM, ATP is capable of inhibiting only 50% of specific [$^{125}$I]APNEA binding, while ADP at the same concentration inhibits only 25% of the specific APNEA binding. App(NH)p, AMP-PCP, 2-methyl-S-AMP, UTP, cAMP and 2-deoxyadenosine all showed <20% inhibition when present at concentrations of 1 mM. In addition, the following ligands failed to compete with labeled APNEA for binding to the A3 receptor protein at concentrations of 100 μM: isoproterenol, carbacol, phentoamine, serotonin and dopamine. These results are inconsistent with the A3 receptor being either a P2 purinergic receptor or other nucleoside/nucleotide binding protein.

Effective competition for labeled APNEA specific binding was found using Gpp(NH)p, a non-hydrolyzable analog of GTP (as shown in FIG. 4B). This compound competed for 60-70% of labeled APNEA binding, with an IC$_{50}$ of 1 μM. A similar effect has been demonstrated on A1 receptor-agonist binding (Stiles et al., ibid.). This effect is distinct from the effect of guanine nucleotides or analogues on A2 receptor-agonist binding (Nanoff et al., 1991, Molec. Pharmacol. 39: 130-135).

The results of ligand binding assays presented herein support the hypothesis drawn from structural data that R226 encodes an novel adenosine receptor, termed A3, and that this receptor exhibits a unique pattern of adenosine receptor ligand binding affinities.

EXAMPLE 5
A3 Adenosine Receptor-Mediated Effects on cAMP Synthesis

The ability of the A3 receptor to couple to second messenger systems in stably transformed CHO cells was determined.

Figure 5:
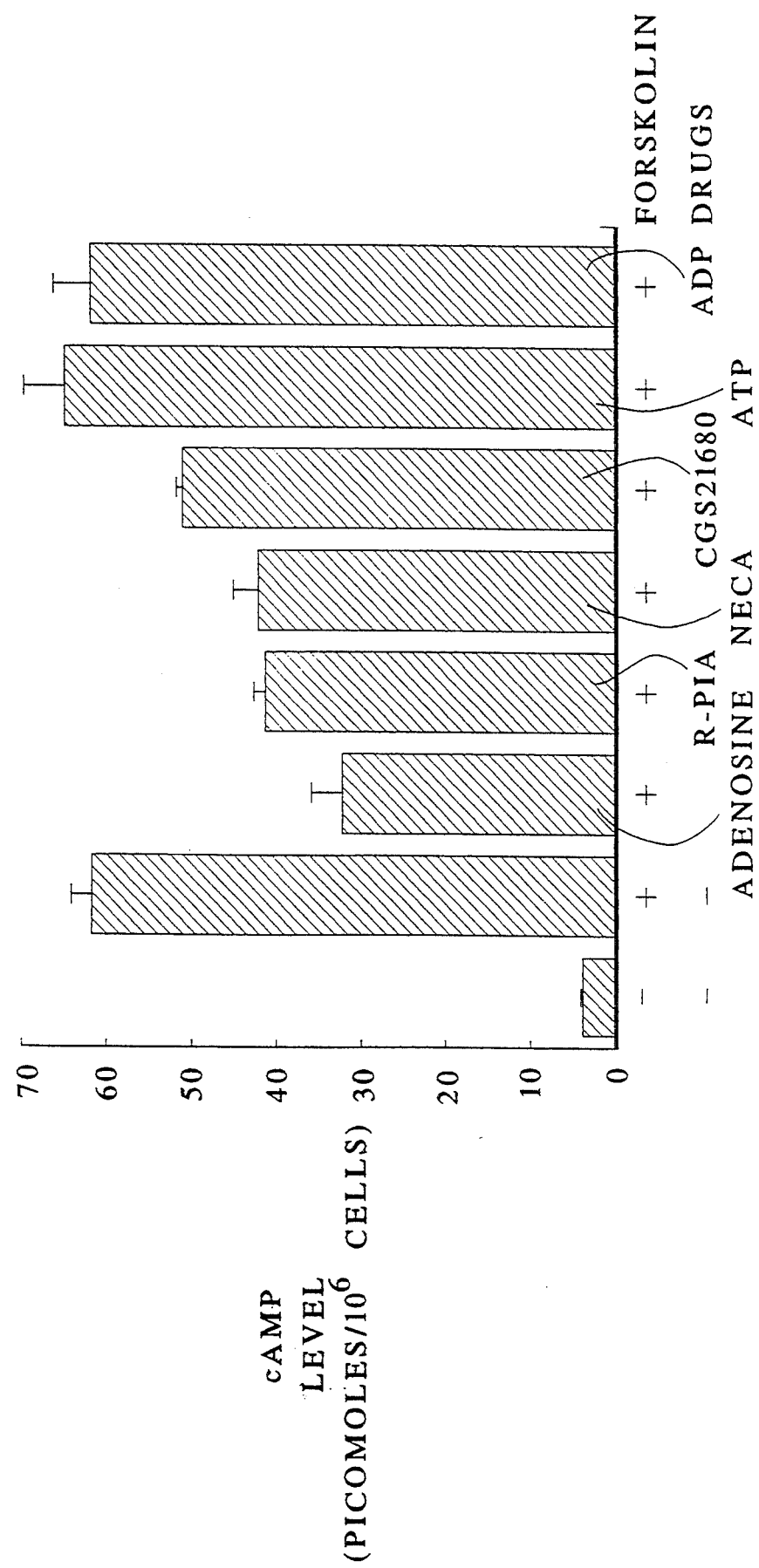
FIG. 5 shows the effects of adenosine agonists on forskolin-stimulated cAMP accumulation in stably transfected CHO cells. The concentrations of adenosine agonists used are 100 nM and the concentration of forskolin is 1 $\mu$M. Values are obtained from triplicate plates and shown as mean ±S.E.

In a first series of experiments, stably transfected CHO cells were used to study the effects of adenosine agonists on cAMP accumulation. It is known that the A1 adenosine receptor inhibits adenylate cyclase activity and the A2 adenosine receptor stimulates adenylate cyclase respectively (Stiles, ibid.; Williams, ibid.). Accumulation of cAMP was measured in the presence of 200 μM Ro 20-1724, a phosphodiesterase inhibitor that is not a derivative of xanthine and therefore thought not to bind to adenosine receptors. In the presence of this phosphodiesterase inhibitor any changes observed in cAMP accumulation should directly reflect changes in cAMP synthesis. The results of these experiments are shown in FIG. 5.

cAMP accumulation experiments were performed as follows. Cells were grown to about 80% confluence in 150 mm dishes, washed twice with Ca$^{++}$ and Mg$^{++}$-free PBS buffer and detached from plates with PBS buffer containing 0.02% EDTA. Cells were collected by centrifugation at 800 rpm (xx g) for 10 min at 4° C. and resuspended in an appropriate volume of KRH buffer [140 mM NaCl, 5 mM KCl, 2 mM CaCl$_2$, 1.2 mM MgSO$_4$, 1.2 mM KH$_2$PO$_4$, 6 mM glucose, 25 mM Hepes-NaOH (pH 7.4)]. The cells were washed once with KRH buffer and resuspended in KRH buffer at a concentration of 10$^7$ cells/ml. Each of 100 μl aliquots of this cell suspension were added to a glass tube containing 100 μl KRH+200 μM Ro 20-1724 and incubated at 37° C. for 10 min. Prewarmed 200 μl KRH containing 200 μm Ro 20-1724 and test drugs were then added to the cells and mixed. After incubation at 37° C. for 20 min, 400 μl 10.5 mM NaAc (pH 6.2) were added and the glass tubes transferred to a boiling water bath. The incubated cell suspension were boiled for 20 min, and the tubes were then cooled to room temperature and centrifuged at 3000 rpm (xx g) for 15 min. 500 μl of the supernatant from each sample were transferred to Eppendorff ™ tubes and 50 μl of the supernatant were assayed for cAMP level, by measuring the ability of cAMP in the sample to displace [8-$^3$H] cAMP from a high affinity cAMP binding protein (Brown et. al., 1971, Biochem. J. 171: 561-562).

For experiments using pertussis toxin pretreatment, aseptic pertussis toxin (Sigma Chemical Co., St. Louis, Mo.) was dissolved in sterile water and added to the medium to a final concentration of 100 ng/ml. Toxin treatment was maintained for approximately 18 hours. The dishes were rinsed once with media immediately prior to the addition of adenosine receptor ligands and processed as described above.

Incubation of wild type and stably transfected CHO cells with 1 μM forskolin resulted in a 15-fold increase in cellular cAMP levels. Addition of the adenosine agonists R-PIA (100 nM), NECA (100 nM), CGS21680 (100 nM), and 100 μM adenosine to stably transfected CHO cells produced 20-50% inhibition of forskolin-stimulated cAMP accumulation (FIG. 5). In wild type CHO cells, on the other hand, adenosine agonists had no effect on forskolin-stimulated cAMP production. Incubation of the cells in the presence of forskolin and ATP and ADP (at a concentration of 100 μM) had no effect. Further experiments showed that inhibition of forskolin-stimulated cAMP production by adenosine agonists was dose-dependent with EC$_{50}$ values (half-maximal inhibition concentration) for each agonist as follows:

TABLE II

| DRUG | EC$_{50}$ |
| --- | --- |
| R-PIA | 18 ± 5.6 nM |
| NECA | 23 ± 3.5 nM |
| CGS 21680 | 144 ± 34 nM |
| Adenosine | 6.5 ± 2.1 μM |

Figure 6:
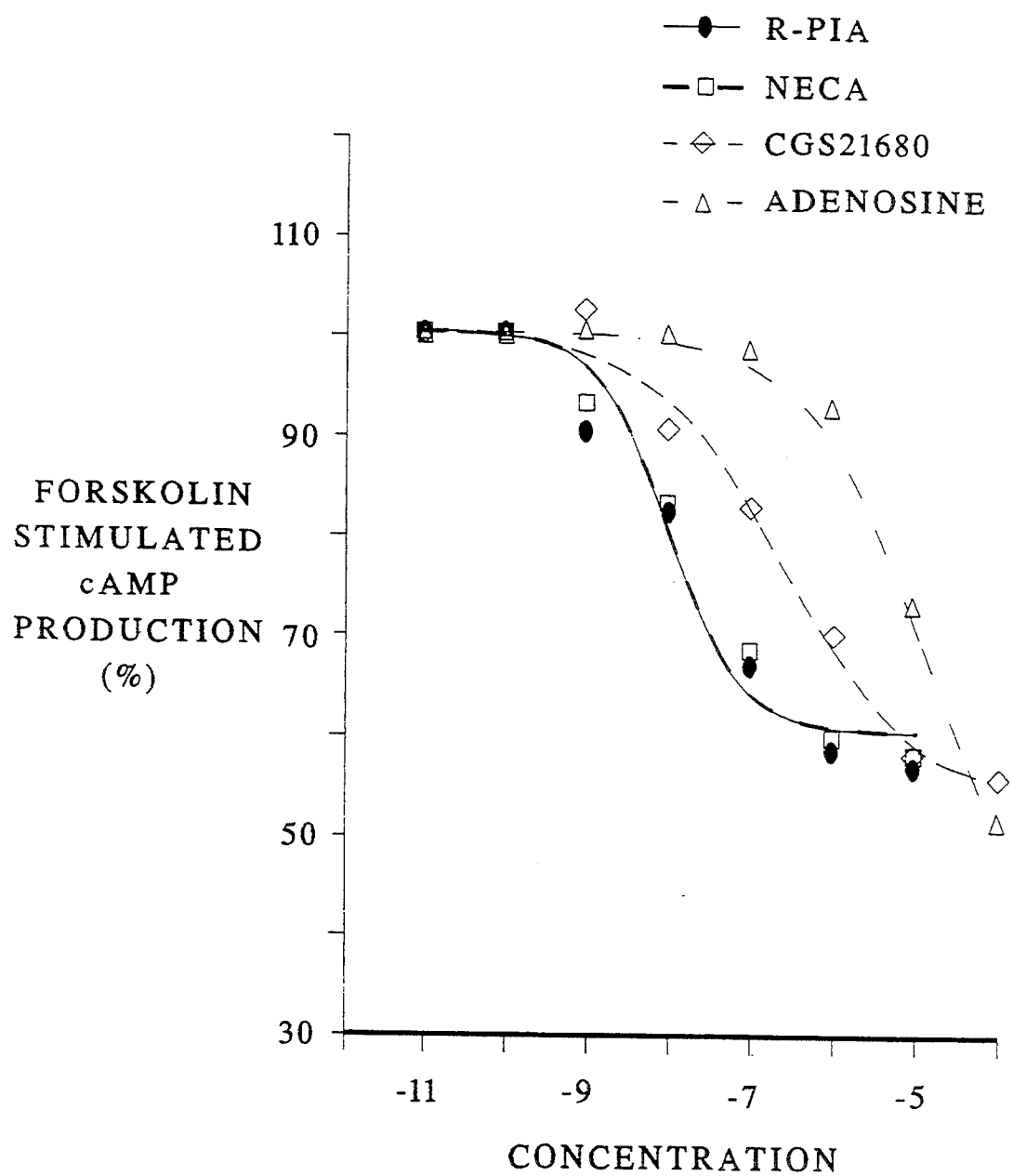
FIG. 6 presents the dose-dependent inhibition by adenosine agonists of forskolin-stimulated cAMP accumulation in stably transfected CHO cells. Results showed as percentage of maximal stimulation of cAMP accumulation observed with 1 $\mu$M forskolin alone.
Figure 7:
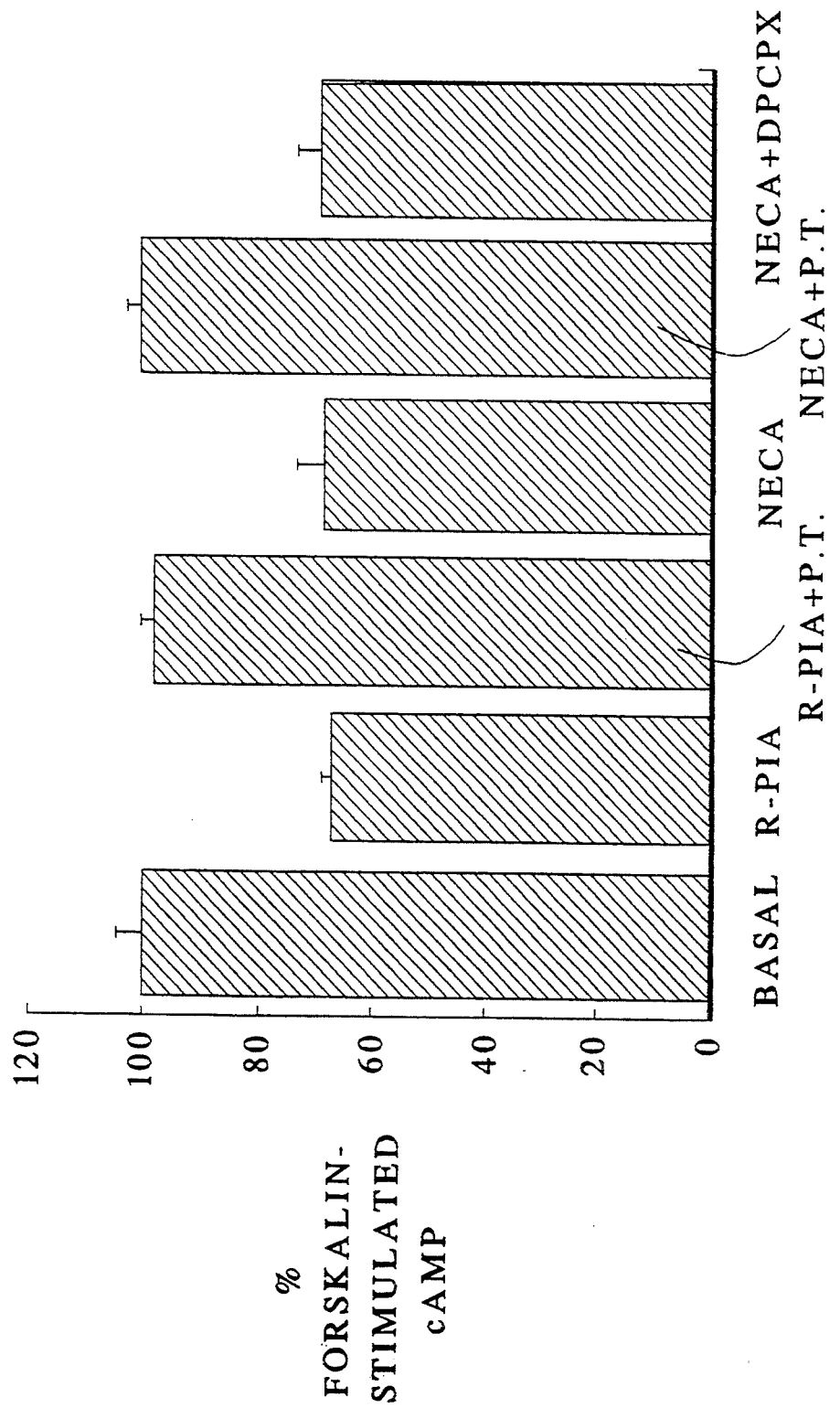
FIG. 7 shows the effects of pertussis toxin pretreatment on forskolin-stimulated cAMP accumulation in stably transfected CHO cells. The results are shown as picomoles cAMP per 10$^6$ cells. The cell were not or pretreated with 100 ng/ml pertussis toxin for 18 hours. The concentration of forskolin and adenosine agonists used are as in FIG. 5.

These results are graphically presented in FIG. 6. R-PIA, NECA and CGS 21680 showed a maximum inhibition of cAMP production from between 40-50% of control values; adenosine does not reach its maximal effect at the concentrations tested. The inhibitory effect of NECA on forskolin-stimulated cAMP production could not be reversed by incubation with 10 nM DPCPX, a very selective A1 adenosine receptor agonist (FIG. 7). This result is in agreement with the binding studies above, showing that radioligand [$^3$H]DPCPX does not bind to the A3 adenosine receptor. These data indicate that the cloned rat adenosine receptor is negatively coupled to adenylate cyclase and is able to reduce forskolin-stimulated cAMP production in CHO cells when its agonist is bound.

We then analyzed whether the inhibition of adenylate cyclase induced by the stimulation of the A3 adenosine receptor is transduced through a pertussis toxin-sensitive G protein. FIG. 7 shows that pretreatment of CHO cell with pertussis toxin almost completely abolished the inhibitory effect of R-PIA and NECA on forskolin-stimulated cAMP production. This result indicates that this novel adenosine receptor inhibits adenylate cyclase through an interaction with a pertussis toxin-sensitive G protein. This conclusion was supported by the observation that [$^{125}$I]APNEA binding could be inhibited by Gpp(NH)p, an unhydrolyzable analogy of GTP (for discussion, see Example 4 above).

On the basis of its pharmacological profile and biochemical activity, the receptor encoded by R226 is an adenosine receptor. This receptor is more similar in its biological properties to the A1 receptor than to the A2 receptor; however, results of the ligand binding experiments described herein demonstrate that this receptor is not A1. The genuineness of R226 as an adenosine receptor is indicated by its ability to recognize adenosine with much higher affinity than ATP, ADP, AMP, cAMP or UTP. We conclude that R226 is a novel adenosine receptor, termed A3, that does not belong to either the A1 or A2 subtypes on the basis of structural (nucleotide and amino acid sequence comparison) and functional (biochemical and pharmacological profile) considerations.

EXAMPLE 6

Tissue Distribution of the A3 Adenosine Receptor

To further gain insight into this novel adenosine receptor, we have examined the tissue distribution of its corresponding mRNA from various tissues by performing PCR on reverse-transcribed cDNA (RT-PCR; Maniatis et al., ibid.). Two primer sequences were chosen that are located in portions of the A3 receptor sequence encoding the N-terminus and the second extracellular loop. These primers were chosen because: (1) they span an intron that is at least 2 kb long, so that possible artifactual amplification of contaminating genomic DNA is avoided; and (2) they are capable of discriminating between amplification of R226 cDNA and amplification of A1 and A2 adenosine receptor cDNAs.

RT-PCR was performed as follows. Total RNA was isolated from different rat tissues as described above. 2 µg total RNA were reverse transcribed by oligo-dT priming in a 20 µl solution containing 50 mM Tris-HCl (pH 8.0), 75 mM KCl, 3 mM MgCl$_2$, 100 mM DTT, 40 Units RNasin, 1 mM dNTPs, and 50 units of murine reverse transcriptase (BRL). cDNA synthesis was performed for 2 hrs at 37° C. The single-stranded cDNA products were denatured by twice heating to 95° C. for 10 min and cooling on ice for 10 min. 1 µl of the single-stranded cDNA products were then subjected to 27 cycles of PCR amplification using these two primers:

(SEQ ID NO: 6)

5' primer (sense): TTCCAGCTGAAGCTTCTC and (SEQ ID NO: 7)

3' primer (antisense): GGTGGAGCTGTTTTGAGA.

Each PCR cycle consisted of denaturing at 95° C. for 45 seconds, annealing at 55° C. for 45 seconds and extending at 72° C. for 90 seconds. PCR products were then run on a 1.2% agarose gel and examined by ethidium bromide staining. A standard curve was developed to ensure linearity of the PCR amplification as follows. pGem226 was linearized by XbaI, and RNA was synthesized with T7 RNA polymerase (BRL). 640, 320, 160, 80, 40, 20, and 10 fg of the in vitro synthesized template RNA were reverse transcribed and PCR amplified as described above. Ethidium bromide staining of the PCR products indicated that the amount of amplified products obtained in RT-PCR amplification of tissue cDNA was approximately proportional to the amount of template added.

Figure 8:
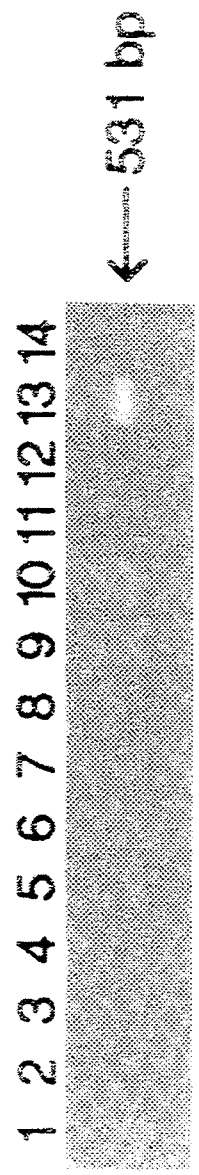
FIG. 8 shows the tissue distribution of A3 receptor transcripts examined by RT-PCR. Lanes 1. striatum, 2. Hippocampus, 3. hypothalamus, 4. pituitary, 5. cortex, 6. olfactory bulb, 7. cerebellum, 8. heart, 9. lung, 10. kidney, 11. liver, 12. adipose tissue, 13. testis, 14. negative control.

The results of these experiments are shown in FIG. 8. Amplification of tissue cDNA using the primers described results in the production of a 531 bp DNA fragment is cells and tissues expressing the A3 adenosine receptor gene. The highest levels of A3 receptor expression were observed in the testis. In addition, moderate levels of expression were observed in the kidneys, lungs and heart. In the central nervous system, low level expression was detected in the cortex, striatum, and olfactory bulb. It is interesting to compare the tissue distribution of the A3 receptor with that of the A1 and A2 receptors. A1 and A2 adenosine receptors are highly expressed in brain regions such as the cerebral cortex, hippocampus, cerebellum, and thalamus (see, Libert et al., 1989, ibid.; Maenhaet et al., 1990, ibid.; Libert et al., 1991, ibid.; Mahan et al., 1991, ibid.; Reppert et al., 1991, ibid. ). In contrast, the A3 receptor is expressed at relatively low levels in the central nervous system and is mainly expressed in peripheral tissues. The high expressions level of A3 found in the testis suggest that adenosine might play a role in reproduction.

It should be understood that the foregoing disclosure emphasizes certain specific embodiments of the invention and that all modifications or alternatives equivalent thereto are within the spirit and scope of the invention as set forth in the appended claims.

---

What we claim is:

1. A cloned nucleic acid having a nucleotide sequence encoding an adenosine receptor, the adenosine receptor having the amino acid sequence in FIG. 1 (SEQ ID NO:4).

2. The cloned nucleic acid of claim 1, wherein the nucleotide sequence consists of the nucleotide sequence in FIG. 1 (SEQ ID NO:3).

3. A nucleic acid probe for the detection of A3 adenosine receptor expression comprising the nucleotide sequence of claim 2.

4. A recombinant expression construct comprising the DNA sequence of claim 1, wherein the construct is capable of expressing the adenosine receptor A3 in a transformed eukaryotic cell culture.

5. The recombinant expression construct of claim 4 comprising sequences selected from the group consisting of pBC12B1 or RcRSV sequences.

6. A recombinant expression construct comprising a nucleotide sequence encoding the adenosine receptor according to claim 1.

7. A eukaryotic cell culture transformed with the expression construct of claim 6, wherein the transform eukaryotic cell culture is capable of expressing the adenosine receptor A3 encoded thereby.

* * * * *

UNITED STATES PATENT AND TRADEMARK OFFICE
CERTIFICATE OF CORRECTION

PATENT NO.  : 5,441,883
DATED       : August 15, 1995
INVENTOR(S) : Civelli et al.

It is certified that error appears in the above-indentified patent and that said Letters Patent is hereby corrected as shown below:

Column 1, line 6 reading "fights" should read --rights--;
Column 1, line 66 reading "Linet al.," should read --Lin et al.,--;
Column 10, line 10 reading "M 13mp18 and M 13mp19" should read
    --M13mp18 and M13mp19--;
Column 10, line 36 reading "and 2.50,000" should read -- and 2. 50,000--;
Column 11, line 49 reading "ofR226" should read --of R226";
Column 13, line 31 reading "(xx g)" this should be deleted;
Column 13, line 36 reading "(xx g)" this should be deleted;
Column 13, line 40 reading "(xx g)" this should be deleted;
Column 13, line 42 reading "(xx g)" this should be deleted;
Column 13, line 49 reading "(xx g)" this should be deleted;
Column 14, line 9 reading "TrisoHCl" should read --Tris-HCl--;
Column 13, line 64 reading "WHAT IS XAC??" should be deleted;
Column 14, line 64 reading "CITE" should be deleted;
Column 14, line 65 reading "[WHAT IS THIS?" should be deleted;
Column 15, line 65 reading "(xx g)" should be deleted; and
Column 16, line 13 reading "(xx g)" should be deleted.

Signed and Sealed this

Seventh Day of May, 1996

Attest:

BRUCE LEHMAN

Attesting Officer

Commissioner of Patents and Trademarks